United States Patent [19]
Pillus et al.

[11] Patent Number: 5,989,897
[45] Date of Patent: Nov. 23, 1999

[54] YEAST SILENCING GENES PROTEINS AND METHODS

[75] Inventors: Lorraine Pillus, Boulder; Astrid Clarke, Longmont; Joanna Lowell, Boulder; Sandra Jacobson, Lafayette; Cheryl Reifsnyder, Boulder, all of Colo.

[73] Assignee: University Technology Corporation, Boulder, Colo.

[21] Appl. No.: 09/047,026

[22] Filed: Mar. 24, 1998

Related U.S. Application Data

[60] Provisional application No. 60/042,375, Mar. 24, 1997.
[51] Int. Cl.$^6$ ............................. C12N 1/19; C12N 1/18; C12N 15/31; C12N 15/63
[52] U.S. Cl. .................................. 435/254.2; 435/254.21; 435/320.1; 536/23.74
[58] Field of Search ...................... 536/23.74; 435/254.2, 435/254.21, 320.1

[56] References Cited

FOREIGN PATENT DOCUMENTS

WO 95/19988  7/1995  WIPO .

OTHER PUBLICATIONS

Abraham, J., et al. "Regulation of Mating–type Information in Yeast" *J. Mol. Biol.*, 176:307–331 (1984).
Aparicio, O.M., et al. "Modifiers of position effect are shared between telomeric and silent mating–type loci in S. cerevisiae," *Cell*, 66:1279–1287 (1991).
Axelrod, A. and Rine, J. "A role for CDC7 in repression of transcription at the silent mating–type locus HMR in Saccharomyces cerevisiae," *Mol. and Cell. Biol.*, 11(2):1080–1091 (1991).
Bassett Jr., D.E., et al. "Yeast genes and human disease," *Nature*, 379:589–590 (1996).
Baudin, A., et al. "A simple and efficient method for direct gene deletion in *Saccharomyces cerevisiae*," *Nucleic Acids Research*, 21(14):3329–3330 (1993).
Borrow, J., et al. "The translocation t(8;16)(p11;p13) of acute myeloid leukaemia fuses a putative acetyltransferase to the CREB–binding protein," *Nature Genetics*, 14:33–41 (1996).
Brachmann, C.B., et al. "The SIR2 gene family, conserved from bacteria to humans, functions in silencing, cell cycle progression, and chromosome stability," *Genes & Dev.*, 9:2888–2902 (1995).
Brand, A.H., et al. "A yeast silencer contains sequences that can promote autonomous plasmid replication and transcriptional activation," *Cell*, 51:709–719 (1987).
Braunstein, M., et al. "Transcriptional silencing in yeast is associated with reduced nucleosome acetylation," *Genes & Dev.*, 7:592–604 (1993).
Brownell, J.E. and Allis, C.D. "Special HATs for special occasions: linking histone acetylation to chromatin assembly and gene activation," *Curr. Opin. in Genes & Devl*, 6:176–184 (1996).

Brownell, J.E. and Allis, C.D. "An activity gel assay detects a single, catalytically active histion acetyltransferase subunits in *Tetrahymena macronuclei*," *Proc. Natl. Acad. Sci. USA*, 92:6364–6368 (1995).
Brownell, J.E., et al. "Tetrahymena histone acetyltransferase A: A homolog to yeast Gcn5p linking histone acetylation to gene activation," *Cell*, 84:843–851 (1996).
Chrivia, J.C., et al. "Phosphorylated CREB binds specifically to the nuclear protein CBP," *Nature*, 365:855–859 (1993).
Dillin, A. and Rine, J. "On the origin of a silencer," *TIBS*, 20:231–235 (1995).
Feldman, J., et al. "Identification of Sites Required for Repression of a Silent Mating Type Locus in Yeast" *J. Mol. Biol.*, 178:815–834 (1984).
Gray, T.E., et al. "Refolding of barnase mutants and pro–barnase in the presence and absence of GroEL," *EMBO J.*, 12(11):4145–4150 (1993).
Greenwell, P.W., et al. "TEL1, a gene involved in controlling telomere length in *S. cerevisiae*, is homologous to the human ataxia telangiectasia gene," *Cell*, 82:823–829 (1995).
Gottschling, D.E., et al. "Position effect at *S. cerevisiae* telomeres: reversible repression of Pol II transcription," *Cell*, 63:751–762 (1990).
Hawthorne, D.C. "A deletion in yeast and its bearing on the structure of the mating type locus," *Genetics*, 48:1727–1729 (1963).
Hebbes, T.R., et al. "A direct link between core histone acetylation and transcriptionally active chromatin," *EMBO J.*, 7(5):1395–1402 (1988).
Hong, L., et al. "Studies of the DNA binding properties of histone H4 amino terminus," *J. Biol. Chem.*, 268(1):305–314 (1993).
Johnson, L.M., et al. "Genetic evidence for an interaction between SIR3 and histone H4 in the repression of the silent mating loci in *Saccharomyces cerevisiae*," *Proc. Natl. Acad. Sci. USA*, 87:6286–6290 (1990).

(List continued on next page.)

*Primary Examiner*—Terry McKelvey
*Attorney, Agent, or Firm*—Greenlee, Winner and Sullivan, PC

[57] ABSTRACT

The present invention provides the yeast genes SAS2, SAS3 and ESA1 and the proteins encoded thereby. SAS2, SAS3 and ESA1 genes of members of the genus Saccharomyces are provided, particularly the SAS2, SAS3 and ESA1 genes of *S. cerevisiae*. Also provided are yeast SAS2, SAS3 and ESA1 coding sequences. Specifically provided are the SAS2, SAS3 and ESA1 coding sequences of members of the genus Saccharomyces, and more specifically of *S. cerevisiae*. Genes of this invention comprise protein coding sequences as well as the regulatory regions that control expression of the encoded protein. Of most interest are SAS2, SAS3, and ESA1 genes of yeast including those of the genus Saccharomyces which are 90% or more homologous to the corresponding genes of *S. cerevisiae*. Specifically provided are DNA constructs comprising purified and isolated DNA molecules comprising SAS2, SAS3 or ESA1 coding sequences that encode proteins from a strain of *S. cerevisiae*.

8 Claims, 6 Drawing Sheets

OTHER PUBLICATIONS

Kamine, J., et al. "Identification of a cellular protein that specifically interacts with the essential cysteine region of the HIV–1 tat transactivator," *Virology*, 216:357–366 (1996).

Kassir, Y., et al. "SAD Mutation of *Saccharomyces cerevisiae* Is an Extra a Cassette"*Mol. Cell. Biol*, 3:871–880 (1983).

Kayne, P.S., et al. "Extremely conserved histone H4 N terminus is dispensable for growth but essential for repressing the silent mating loci in yeast," *Cell*, 55:27–39 (1988).

Kennedy, B.K., et al. "Mutation in the silencing gene SIR4 can delay aging in *S. cerevisiae*," *Cell*, 80:485–496 (1995).

Kimmerly, W., et al. "Roles of two DNA–binding factors in replication, segregation and transcriptional represion mediated by a yeast silencer" *EMBO J.*, 7:2241–2253 (1988).

Kleff, S., et al. "Identification of a gene encoding a yeast histone H4 acetyltransferase," *J. Biol. Chem.*, 270(42):24674–24677 (1995).

Lee, D.Y., et al. "A positive role for histone acetylation in trnascription factor access to nucleosomal DNA," *Cell*, 72:73–84 (1993).

Lee, F–J., et al. "Acetylation is required for normal growth and mating of *Saccharomyces cerevisiae*," *J. Bacteriol.*, 171(11):5795–5802 (1989).

Loo, S. and Rine, J. "Silencing and heritable domains of gene expression," *Annu. Rev. Cell Dev. Biol.*, 11:519–548 (1995).

Mahoney, D.J., et al. "Mutations in the HML E silencer of *Saccharomyces cerevisiae* yield metastable inheritance of transcriptional repression," *Genes & Dev.*, 5:605–615 (1991).

Marcus, G.A., et al. "Functional similarity and physical association between GCN5 and ADA2: putative transcriptional adaptors," *EMBO J.*, 13(20):4807–4815 (1994).

Megee, P.C., et al. "Genetic analysis of histone H4: essential role of lysines subject to reversible acetylation," *Science*, 247:841–845 (1990).

Morrow, D.M., et al. "TEL1, and *S. cerevisiae* homolog of the human gene mutated ataxia telangiectasia, is functionally related to the yeast checkpoint gene MEC1," *Cell*, 82:831–840 (1995).

Mullen, J.R., et al. "Identification and characterization of genes and mutants for an N–terminal acetyltransferase from yeast," *EMBO J*, 8(7):2067–2075 (1989).

Ehrenhofer–Murray, A.E., et al. "The role of Sas2, an acetyltransferase homologue of *Saccharomyces cerevisiae*, in silencing and ORC function," *Genetics*, 145:923–934 (1997).

Park, E–C. and Szostak, J.W. "Point mutations in the yeast histone H4 gene prevent silencing of the silent mating type locus HML," *Mol. Cell. Biol.*, 10(9):4932–4934 (1990).

Parthun, M.R., et al. "The major cytoplasmic histone acetyltransferase in yeast: links to chromatin replication and histone metabolism," *Cell*, 87:85–94 (1996).

Pennisi, E. "Opening the way to gene activity," *Science*, 275:155–157 (1997).

Pillus, L. and Grunstein, M. "Chromatin structure and epigenetic regulation in yeast" *Chromatin Structure and Gene Expression* (ed. Elgin, S.C.R.) IRL Press, Oxford University Press, pp. 123–146 (1995).

Pillus, L. and Rine, J. "Epigenetic inheritance of transcriptional states in *S. cerevisiae*," *Cell*, 59:637–647 (1989).

Reifsnyder, C., et al. "Yeast SAS silencing genes and human genes associated with AML and HIV–1 Tat interactions are homologous with acetyltransferases," *Nature Genetics*, 14:42–49 (1996).

Renauld, H., et al. "Silent domains are assembled continously from the telomere and are defined by promoter distance and strength, and by SIR3 dosage," *Genes & Dev.*, 7:1133–1145 (1993).

Roth, S.Y. and Allis, C.D. "Histone acetylation and chromatin assembly: a single escort, multiple dances?" 87:5–8 (1996).

Roth, S.Y. "Something about silencing," *Nature Genetics*, 14:3–4 (1996).

Rothstein, R. "Targeting, disruption, replacement, and allele rescue: integrative DNA transformation in yeast," *Meth. Enzymol.*, 194:281–301 (1991).

Savitsky, K, et al. "A single ataxia telangiectasia gene with a product similar to Pl–3 kinase," *Science*, 268:1749–1753 (1995).

Scherens, B., et al. "Sequencing and functional analysis of a 32560 bp segment on the laft arm of yeast chromosome II. Identification of 26 open reading frames, including the KIP1 and SEC17," *Yeast*, 9:1355–1371 (1993).

Schrader, A. "Genes in baker's yeast may aid HIV research," *The Denver Post*, Sep. 3, 1996.

Shaw, W.V. and Leslie, A.G.W. "Chloramphenicol acetyltransferase," *Annu. Rev. Biophys. Chem*, 20:363–386 (1991).

Spencer, F., et al. "Mitotic chromosome transmission fidelity mutants in *Saccharomyces cerevisiae*," *Genetics*, 124:237–249 (1990).

Strathern, J.N., et al. "Isolation of a circular derivative of yeast chromosome III: Implications for the mechanism of mating type interconversion," *Cell*, 18:309–319 (1979).

Sussel, L., et al. "Epigenetic switching of transcriptional states: cis– and trans–acting factors affecting establishment of silencing at the HMR locus in *Saccharomyces cerevisiae*," *Mol. Cell. Biol.*, 13(7):3919–3928 (1993).

Taunton, J., et al. "A mammalian histone deacetylase related to the yeast transcriptional regulator Rpd3p," *Science*, 272:408–411 (1996).

Tercero, J.C. and Wickner, R.B. "MAK3 encodes an N–acetyltransferase whose modification of the L–A gag $NH_2$ terminus is necessary for virus particle assembly," *J. Biol. Chem.*, 267(28):20277–20281 (1992).

Thompson, J.S., et al. "Histone H3 amino terminus is required for telomeric and silent mating locus repression in yeast," *Nature*, 369:245–247 (1994).

Orr–Weaver, T.L., et al. "Gene conversion adjacent to regions of double–strand break repair," *Mol. Cell. Biol.*, 8(12):5292–5298 (1988).

Whiteway, M., et al. "The yeast ARD1 gene product is required for repression of cryptic mating–type information at the HML locus," 7(10):3713–3722 (1987).

```
SAS2    GKGKNKPSAK IKKTQKEMLY GILNERNIRQ IQFGLNKKFS TWYGSAVYFD  72
SAS3    LTFLENSKSA TYINGNVSLC NHNETDQENE DRKKRKGKVP RIKNKVWFSQ 271
Esa1p   .......... ....SGSMT  QNP...HEVA RVRN...... ..........  166
Sp sas+ KTVADRTKDV AYSFSDPILS TQLRTPP..P QPTS...... .......... 102
TIP60   .......... ....MTGSLV SDRSHDDIVT RMKN...... ..........  20
MOZ     EIMTEKDMEL FRDIQEQALQ KVGVTGPPDP QVRC...... .......... 508

*  *              *
SAS2    PETKRLGCSE TKGQLSSVSN SQYW.LDTLF VCEYCFKYTD DQTRFVGHVA 121
SAS3    IEYIVLRNYE IKPWYTSPFP EHINQNKMVF ICEFCLKYMT SRYTFYRHQL 321
244w    LNRIIMGKYE IEPWYFSPYP IELTDEDFIY IDDFTLQYFG SKKQYERYRK 216
Esa1p   IRYLYFGTYR IKPWYTSPYP EEYSCAKNLY ICESCLKYMN SDHVLQRHKM 152
TIP60   IECIELGRHR LKPWYFSPYP QELTTLPVLY LCEFCLKYGR SLKCLQRHLT  70
MOZ     PSVIEFGKYE IHTWISSPYP QEYSRLPKLY LCEFCLKYMK SRTILQQHMK 558

*
SAS2    SCPFQYRVPG KIKYKSPEYT IRRVKGSKYQ LFCQCLCLFT KLYLDNKSMY 171
SAS3    KCLT.FKPPG NEIYRDGKLS VWEIDGRENV LYCQNLCLLA KCFINSKTLY 370
Esa1p   KCTL.RHPPG NEIYRDDYVS FFEIDGRKQR TWCRNLCLLS KLFLDHKTLY 265
Sp sas+ KCSW.SYPPG DEIYRDKNIS IFEVDGQRQP IYCQNLCLLA KMFLHSKMLY 201
TIP60   KCDL.RHPPG NEIYRKGTIS FFEIDGRKNK SYSQNLCLLA KCFLDHKTLY 119
MOZ     KCGW.FHPPA NEIYRKNNIS VFEVDGNVST IYCQNLCLLA KLFLDHKTLY 608

SAS2    FKVDHYEFYI VYETGST... ........KP MGFFSKDLVS YQQNNLACIL 210
SAS3    YDVEPFIFYI LTEREDTENH PYQNAAKFHF VGYFSKEKFN SNDYNLSCIL 420
Esa1p   YDVDPFLFYC MTRRDELG.. ........HHL VGYFSKEKES ADGYNVACIL 306
Sp sas+ YDVEPFLFYV LTEFDGQE.. ........CKV IGYFSKEKRS ASDYNVSCIL 242
TIP60   YDTDPFLFYV MTEYDCKG.. ........FHI VGYFSKEKES TEDYNVACIL 160
MOZ     YDVEPFLFYV LTQNDVKG.. ........CHL VGYFSKEKHC QQKYNVSCIM 648

SAS2    IFPPYQRRGL GLLIEFSYK LSQLEGVISG PEVPLSPFGL IGYLKYWSQI 260
SAS3    TLPIYQRKGY GQFLMEFSYL LSRKESKFGT PEKPLSDLGL LTYRTFWKIK 470
Esa1p   TLPQYQRMGY GKLLIEFSYE LSKKENKVGS PEKPLSDLGL LSYRAYWSDT 356
Sp sas+ TLPIYQRRGY GVFLIDFSYL LTQVEGKLGS PEKPLSDLGL VTYRSYWKMR 292
TIP60   TLPPYQRRGY RKLLIEFSYE LSKVEGKTGT PEKPLSDLGL LSYRSYWSQT 210
MOZ     ILPQYQRKGY GRFLIDFSYL LSKREGQAGS PEKPLSDLGR LSYMAYWKSV 698

SAS2    LCWHLIE... ........GD LAHYDKVTLE DLSIVTGMRV NDVILTLKHL 299
SAS3    CAEVLLKLRD SARRRSNNKN EDTFQQVSLN DIAKLTGMIP TDVVFGLEQL 520
Esa1p   LITLLVEHQK E......... ....ITID EISSMTSMTT TDILHTAKTL 391
Sp sas+ VAKALLEIT. .....T.... ....PISIN AIAKSTSMVC DDVISTLESL 327
TIP60   ILEILMGLKS ESGERP.... .....QITIN EISEITSIKK EDVISTLQYL 251
MOZ     ILECLY.... .HQNDK.... .....QISIK KLSKLTGICP QDITSTLHHL 734

SAS2    NCI....... ..GENNQIYL QSLNSWLKLH GTKRNW.... ..FKLKDEYL 334
SAS3    QVLYRHKTRS LSSLDDFNYI IKIDSWNRIE NIYKTWSSKN YP.RVKYDKL 569
Esa1p   NILRY..YKG ......QHI IFLNEDILDR Y..NRLKAKK RRTIDPNRLI 330
Sp sas+ SVFKYDPLKK ......KYV LQL.KRDELE NVYKAWNIK. HPQRVNPKLL 368
TIP60   NLINY..YKG ......QYI LTL.SEDIVD GHERAMLKRL ..LRIDSKCL 289
MOZ     RMLDF..RSD ......QFV IIR.REKLIQ DHMAKLQLNL RPVDVDPECL 774

SAS2    LIDD......  338
SAS3    LWEPIILGPS  579
Esa1p   WKPPVFTASQ  340
Sp sas+ RWTPYLGEEQ  378
TIP60   HFTPKDWSKR  299
MOZ     RWTPVIVSNS  784
```

FIG. 2

| SIR1 | SAS2 | SAS3 | Growth | Mating |
|---|---|---|---|---|
| + | + | + |  | 1.00 |
| − | + | + |  | 0.56 |
| + | − | + |  | 0.44 |
| + | + | − |  | 1.08 |
| − | − | + |  | $6.92 \times 10^{-3}$ |
| − | + | − |  | 0.16 |
| + | − | − |  | 1.18 |
| − | − | − |  | $2.15 \times 10^{-4}$ |

YEAST SILENCING GENES PROTEINS AND METHODS

CROSS-REFERENCE TO RELATED APPLICATION

This application claims the benefit of U.S. Provisional Application Ser. No. 60/042,375, filed Mar. 24, 1997.

STATEMENT REGARDING FEDERALLY SPONSORED RESEARCH OR DEVELOPMENT

This invention was made, at least in part, with funding from the National Science Foundation (Grant No. 1533408). Accordingly, the United States Government has certain rights in this invention.

FIELD OF INVENTION

This invention relates to the field of genetics. This invention relates generally to silencing of genes. It further relates to methods for screening agents for their therapeutic potential in treating AML (acute myeloid leukemia) and AIDS (acquired immune deficiency syndrome).

BACKGROUND OF THE INVENTION

Silencing is an epigenetic form of transcriptional regulation in eukaryotes in which certain regions of chromosomes, e.g., certain genes, are made into transcriptionally inactive chromatin structures. [For reviews, see Loo, S. et al. (1995) Annu. Rev. Cell Dev. Biol. 11: 519–548 and Pillus, L. and Grunstein, M. Chromatin Structure and Gene Expression (ed. Elgin, S. C. R.) (1995) IRL Press, Oxford University Press, pp. 123–146.] Silencers, which are specialized regulatory sites in DNA, and various proteins, including general DNA-binding proteins and silencing proteins, are responsible for silencing. Silencing is related, in part, to the (degree of) acetylation of histones, especially histone H4.

Silencing appears to involve at least three distinct phases or processes: establishment, maintenance, and inheritance. Establishment refers to the genetic switch from active to silenced (inactive) chromatin. Maintenance refers to the continuation of the silenced state of the chromatin. Inheritance refers to the propagation of the silenced state as the chromatin is replicated.

In *Saccharomyces cerevisiae*, a number of proteins and genes involved in silencing have been identified. Silencing in yeast is integral to yeast mating-type biology.

Yeast mating-type is determined by the allele present at the mating-type locus, MAT, located near the center of chromosome III. Cells of *Saccharomyces cerevisiae* can be one of three types: a haploid, α haploid, or a/α diploid. Cells with the a allele at the MAT locus are of the a mating-type. Cells with the α allele at the MAT locus are of the α mating-type. The MATa and MATα alleles encode regulatory proteins which control genes specifying the functional differences between a and α cell types. Opposite type haploid cells can mate with one another to form diploid cells. The simultaneous expression of MATa and MATα alleles leads to disruption of normal haploid cell functions, including the ability to mate.

In addition to the transcriptionally active MAT locus, *S. cerevisiae* cells also contain silenced (i.e., transcriptionally inactive) copies of the a and α genes at two other loci, HML and HMR, which are located near opposite ends of chromosome III. Upon transposition of an a and α allele from HML or HMR to MAT, yeast switch from a to α, or vice versa. In haploid cells the silent mating-type loci are repressed. If these loci are not repressed, the simultaneous expression of a and α leads to the non-mating phenotype of a/α diploid cells.

Repression of the silent mating-type loci involves regulatory sites adjacent to HML and HMR [Hawthorne, D. (1963) *Genetics*, 48:1727–1729; Kassir, Y. et al. (1983) *Mol. Cell. Biol.* 3:871–880; Strathern, J. et al. (1979) *Cell* 18:309–319; Abraham, J. et al. (1984) *J. Mol. Biol.* 176:307–331; Feldman, J. et al. (1984) J. Mol. Biol. 178: 815–834]. The HML-flanking silencers are HM-E and HML-I; the HMR-flanking silencers are HMR-E and HMR-I. The E and I silencers comprise elements corresponding to an autonomously replicating sequence (ARS) consensus sequence, and Rap1p- and Abf1-protein binding sites [Brand, A. et al. (1987) *Cell* 51:709–719].

Four SIR (silent information regulator) genes silence HML and HMR [Haber, J. et al. (1979) *Genetics* 93:13–35; Klar, A. et al. (1979) *Genetics* 93:37–50; Rine, J. et al. (1987) *Genetics* 116:9–22; Rine, J. et al. (1979) *Genetics* 93:877–901].

SIR1 encodes the Sir1p protein, which is thought to play a role in establishment of silencing at the silent mating-type loci, HML and HMR; Sir1p is not involved in maintenance or propagation of silencing. Mutant sir1 cells are deficient in establishing silencing; however, after silencing is established, these mutant cells maintain and propagate the silenced state at HML and HMR [Pillus, L. et al. (1989) *Cell* 59:637–647].

SIR2 encodes the Sir2p protein, which is thought to be required for silencing. Cells with sir2 mutations are not only deficient in silencing, but also have an elevated level of recombination in ribosomal DNA [Gottlieb, S. et al. (1989) *Cell* 56: 771–776]. Sir2P also appears to play a role in acetylation of histones. Evidence suggests that Sir2p is, or regulates, a deacetylase or that it inhibits a histone acetyltransferase. Overproduction of Sir2p results in decreased acetylation of core histones H2B, H3 and H4 [Braunstein, M. et al. (1993) *Genes Dev.* 7:592–604].

SIR3 encodes the Sir3p protein, which is also required for silencing. Cells with sir3 mutations are deficient in silencing, and have increased rates of mitotic recombination [Palladino, F. et al. (1993) *Cell* 75:543–555]. Sir3p can form a stable complex with a protein (Rap1p) involved in DNA repair [Paetkau, D. et al. (1994) *Genes Dev.* 8:2035–2045]; hence Sir3p is thought to be involved in DNA repair as well as in silencing. Increasing SIR3 gene dosage leads to increased silencing [Renauld, H. et al. (1993) *Genes Dev.* 7:1133–1145]. Cells without Sir3p are completely deficient in silencing [Aparicio, O. et al. D. (1991) *Cell* 66:1279–1287; Rine, J. et al. (1987) *Genetics* 116:9–22].

SIR4 encodes the Sir4p protein, also absolutely necessary for silencing. Cells with sir4 null mutations are deficient in silencing, and have a fourfold increase in chromosomal loss. SIR4 is postulated to encode a structural component of chromosomes [Palladino, F. et al. S. (1993) *Cell* 75:543–555].

The Sir2, Sir3, and Sir4 proteins are also required for telomeric silencing, another type of silencing in *S. cerevisiae* which has many similarities to mating-type loci silencing. Null mutations in SIR2, SIR3, or SIR4 result in total loss of silencing, both mating-type loci and telomeric silencing. Sir1p, unlike the proteins encoded by SIR2, SIR3, and SIR4, is not necessary for silencing at the silent mating-type loci and apparently has no function at telomeres. Mutations in the SIR genes do not affect cell viability.

Evidence indicates that local chromatin structure is involved in regulation of silencing. The positively charged N-terminal regions of histones H3 and H4 are believed to facilitate silencing via both compaction of chromatin and through specific interactions with silencing proteins. Intact N-termini of histones H3 and H4 are required for complete silencing of HML and HMR [Thompson, J. et al. (1994) *Nature* 369:245–247; Johnson, L. et al. (1990) *Proc. Natl. Acad. Sci. USA* 87:6286–6290; Kayne, P. et al. (1988) *Cell* 55:27–39; Megee, P. et al. (1990) *Science* 247:841–845; Park, E. et al. (1990) *Mol. Cell. Biol.* 10:4932–4934]. The positive charges of the N-termini of histones H3 and H4 appear to be important to their role in silencing. The DNA-binding properties of histones H3 and H4 are altered if the lysines in the N-termini are acetylated [Hong, L. et al. (1993) *J. Biol. Chem.* 268:305–314].

The N-termini of histones H3 and H4 are often highly acetylated in transcriptionally active regions [Hebbes, T. et al. (1988) *EMBO J.* 7: 1395–1402; Lee, D. et al. (1993) *Cell* 72:73–84], and unacetylated in transcriptionally inactive (silenced) regions [Pillus, L. et al. in *Chromatin Structure and Gene Expression* (ed. Elgin, S. C. R.) (1995) IRL Press, Oxford University Press pp. 123–146]. Different patterns of acetylation are seen in heterochromatin versus euchromatin, as shown by immunological reagents directed to differentially acetylated lysines in the N-terminal regions of histone H4 [Turner, B. et al. (1992) *Cell* 69:375; Bone, J. et al. (1994) *Genes Dev.* 8: 96]. The H4 histones of the inactive X chromosome (Barr bodies) in female mammals are not acetylated [Jeppesen, P. et al. (1993) *Cell* 74: 281].

It is thought that acetylated histones bind DNA less tightly, making DNA more accessible to proteins involved in gene expression. Four nuclear histone acetylating enzymes and five deacetylating enzymes were recently reviewed [Pennisi, E. (1997) *Science* 275: 155–157]. Histone acetylases include: Tetrahymena, *S. cerevisiae*, and human HAT A (Gcn5p); human PCAF; human p300/CBP; and human, Drosophila, and *S. cerevisiae* TAF$_{II}$230/250. Histone deacetylases include: human, Drosophila, *S. cerevisiae*, and possibly Xenopus, mouse and nematode DHAC1 (RPD3); *S. cerevisiae* HDA1; *S. cerevisiae* HOS1; *S. cerevisiae* HOS2; and *S. cerevisiae* HOS3.

Because acetylation of histones affects gene expression, it is thought to affect cell cycle and proliferation, and therefore malfunctions of these processes can result in cancer. For example, trapoxin, a potential anti-cancer agent, inhibits cell growth and makes cancer cells revert to their normal, differentiated state. Trapoxin also inhibits histone deacetylation [Taunton, J. et al. (1996) *Science* 272: 408]. Blocking the removal of acetyl groups from histones is believed to be responsible for trapoxin's anti-tumor effect by restoring normal gene expression, e.g., transcription of a tumor-suppressor gene.

The present invention identifies novel genes encoding silencing proteins in *S. cerevisiae*. It further provides the proteins encoded by these genes. It also provides methods of using these genes and proteins in a screen for drugs useful in the treatment of mammalian, particularly human, diseases. It specifically provides a method of using mutant strains of *S. cerevisiae* in a method for screening agents for their ability to affect Tip60 expression and/or activity [Kamine, J. et al. (1996) *Virology* 216:357–366] and for their ability to affect the 5' translocation partner (protein) of the MOZ-CBP (monocytic leukemia zinc finger protein-CREB binding protein) chimeric oncogene [Borrow, J. et al. (1996) *Nature Genet.* 14:33–41].

The HIV-1 protein Tat is necessary for HIV replication and is a strong transactivator of HIV gene expression. Tip60, a 60 kDa protein which interacts with the cysteine-rich region of Tat, is postulated to be a cofactor of Tat-dependent regulation of gene expression in HIV [Kamine, J. et al. (1996) *Virology* 216:357–366]. Overexpression of Tip60 results in a fourfold increase of Tat transactivation of the HIV-1 promoter in transient expression assays. Nothing is known about the regulation of Tip60 in vivo.

The translocation t(8;16)(p11;p13) found in 4–7 patients per 1,000 patients with acute myeloid leukemia (AML) fuses the MOZ gene to the gene encoding the CREB-binding protein [Borrow, J. et al. (1996) *Nature Genet.* 14:3314 41]. The CREB-binding protein is a transcriptional coactivator which connects the basal transcriptional machinery to other transcription factors. Moz (monocytic leukemia zinc finger protein) is a putative chromatin-bound acetyltransferase. Moz contains two C4HC3 (four cysteines, one histidine, three cysteines) zinc fingers, a C2CH (two cysteines, one cysteine, one histidine) zinc finger and an acetyltransferase consensus domain. The Moz-CBP oncoprotein may mediate leukemogenesis via abnormal acetylation of chromatin at promoters which require CBP bridging. This abnormal acetylation may thereby abnormally acetylate genes whose expression is inappropriate for normal hematopoiesis.

There is as long-felt need in the art for methods of screening agents for their usefulness in the treatment of AIDS and acute myeloid leukemia. Such needed methods are quick, inexpensive and easy to carry out compared to existing methods which do not focus on the genetic basis of these diseases, including tests on animal models.

SUMMARY OF THE INVENTION

The present invention provides the yeast genes SAS2, SAS3 and ESA1 and the proteins encoded thereby. The ScYO244w gene of U.S. provisional application 60/042, 375, filed Mar. 24, 1997 is herein referred to and renamed EAS1. SAS2, SAS3 and ESA1 genes of members of the genus Saccharomyces are provided, particularly the SAS2, SAS3 and ESA1 genes of *S. cerevisiae*. Also provided are yeast SAS2, SAS3 and ESA1 coding sequences. Specifically provided are the SAS2, SAS3 and ESA1 coding sequences of members of the genus Saccharomyces, and more specifically of *S. cerevisiae*. Genes of this invention comprise protein coding sequences as well as the regulatory regions that control expression of the encoded protein. Of most interest are SAS2, SAS3, and ESA1 genes of yeast including those of the genus Saccharomyces which are 90% or more homologous to the corresponding genes of *S. cerevisiae*. Specifically provided are DNA constructs comprising purified and isolated DNA molecules comprising SAS2, SAS3 or ESA1 coding sequences that encode proteins from a strain of *S. cerevisiae*.

The nucleotide sequence for the coding strand of SAS2 is given in SEQ ID NO:1, and the protein coding sequence extends between nucleotides 1712 and 2728, exclusive of the translation termination codon. The nucleotide sequence for SAS3 is given in SEQ ID NO:3, and the protein coding sequence extends between nucleotides 1340 and 3832, exclusive of the translation termination codon. The nucleotide sequence for EAS1 is given in SEQ ID NO:5, and the protein coding sequence extends between nucleotides 531 and 1865, exclusive of the translation termination codon. Provided are SAS2, SAS3 and EAS1 genes of yeast, including those of the genus Saccharomyces, which genes have 20% or greater nucleotide sequence identity with the corresponding genes of *S. cerevisiae*. Also provided are SAS2, SAS3 and ESA1 genes of yeast including those of the genus Saccharomyces, which genes have 35% or greater nucleotide sequence identity with the corresponding genes of S. cerevisiae. Additional, provided are SAS2, SAS3 and ESA1 genes of yeast including those of the genus Saccharomyces, which genes have 50% or greater nucleotide sequence identity with the corresponding genes of S. cerevisiae. Of more interest are SAS2, SAS3 and ESA1 genes of yeast including those of the genus Saccharomyces, which genes have 70% or greater nucleotide sequence identity with the corresponding genes of S. cerevisiae. Of most interest are SAS2, SAS3 and ESA1 genes of yeast including those of the genus Saccharomyces, which genes have 80% or greater, 85% or greater, or 95% or greater nucleotide sequence identity with the corresponding genes of S. cerevisiae. The sequences for S. cerevisiae, SAS2, SAS3 and ESA1 genes are in SEQ ID Nos: 1, 3 and 5. It will be understood by those in the art that among various species of Saccharomyces there can be minor sequence variations.

This invention specifically provides proteins which are products of the coding sequences of this invention. More specifically provided are Sas2p, Sas3p, and Esa1p. Silencing proteins are products of genes which make certain regions of chromosomes transcriptionally inactive. The amino acid sequence for Sas2p of S. cerevisiae is given in SEQ ID NO:2. The amino acid sequence for Sas3p of S. cerevisiae is given in SEQ ID NO:4. The amino acid sequence for Esa1p of S. cerevisiae is given in SEQ ID NO:6.

This invention encompasses nucleotide sequences which encode yeast Sas2p, Sas3p and Esa1p, and particularly those of Saccharomyces. This invention particularly encompasses nucleotide sequences which encode the amino acid sequences of SEQ ID NO: 2, SEQ ID NO: 4, and SEQ ID NO: 6.

It is a further purpose of this invention to provide DNA constructs comprising a yeast SAS2 gene, a yeast SAS3 gene, or a yeast ESA1 gene. Constructs comprising Saccharomyces SAS2, SAS3 or ESA1 genes are provided by the present invention. This invention provides DNA constructs comprising the nucleotide sequences of S. cerevisiae SAS2, S. cerevisiae SAS3 and S. cerevisiae ESA1 .

The DNA constructs of this invention also encompass the coding sequences of yeast, including yeast of the genus Saccharomyces, SAS2, SAS3, or ESA1 genes with appropriate regulatory sequences for expression of the coding sequences in the host cell. The coding sequences of yeast SAS2, SAS3, or ESA1 genes can be readily introduced into vectors with regulatory sequences to direct expression in a desired host cell. Preferred host cells are yeast cells, including yeasts of the genus Saccharomyces. This invention also includes mutant sequences of SAS2, SAS3, and ESA1, such as those in strains LPY2879, LPY2889, and LPY2877, as discussed below.

It is a further purpose of this invention to provide a method for screening agents for their ability to affect Tip60, which is a protein which interacts with the HIV-1 Tat protein, and for their ability to affect the 5' translocation partner of the Moz-CBP (monocytic leukemia zinc finger protein-CREB binding protein) chimeric oncogene. Three other human genes, R96016, Z25309 and H11938, are homologues of the yeast genes of this invention. The function(s) of these five human genes is not understood fully. We believe that these human genes are useful in screening agents to treat mammalian diseases besides AIDS and acute myeloid leukemia, particularly other forms of leukemia. Mutant strains of yeast containing these human genes can be used to screen agents for their ability to treat human diseases. We believe that the function(s) of these human genes and other mammalian genes of this gene family can be determined by transferring them into mutant yeast strains and then monitoring such strains for phenotypes, e.g. viability and temperature sensitivity, under various conditions and in the presence and absence of various reporter genes and potentially modulating test agents or compounds.

This invention further provides novel strains of yeast employed in the methods described herein. Reproducible methods for isolating desired mutant yeast strains, particularly Saccharomyces mutant strains and S. cerevisiae mutants strains, are provided. Mutant yeast strains can be identified by the presence of a detectable mutant phenotype. Detectable phenotypes can be detected qualitatively and/or quantitatively and include but are not limited to decreased viability, temperature sensitivity, decreased mating ability, expression or lack thereof of reporter genes and/or selectable markers, etc.

This method comprises cultivating strains of yeast according to the present invention in the presence of an agent and measuring the level of expression of a preselected gene, including specifically reporter genes. Yeast strains of the present invention include those with mutations in the SIR1, SAS2, SAS3, and/or ESA1 genes. Particularly, yeast strains of this invention include MATa sir1 sas2 mutants, MATa sir1 sas3 mutants, and MATa sir1 sas2 sas3 mutants, all of which have phenotypes of decreased mating ability. More particularly, yeast strains of this invention include MATa sir1 sas2 mutants, MATa sir1 sas3 mutants, and MATa sir1 sas2 sas3 mutants, which contain a selectable marker or reporter gene at the mating-type loci or at telomere-proximal loci. Also included in the strains of this invention are those having nat1 and ard1 mutations in combination with sas2 mutations. Particularly of interest are mutant strains of Saccharomyces, especially mutant strains of S. cerevisiae.

Most particularly, yeast strains of this invention include those with mutations in ESA1, particularly strains with point mutations in ESA1 having the phenotype of temperature sensitivity, i.e., they are not viable at temperatures as high as the wild-type.

ESA1 has greater similarity to the human genes Tip60 and MOZ-CBP, than have SAS2 and SAS3. ESA1 is therefore the most preferred of the genes of this invention for use in screening agents to identify those which may be useful in treating AML and AIDS. Unlike SAS2 and SAS3, ESA1 is essential for yeast viability, indicating that it provides a critical function for the cell. Of most importance are ESA1 mutants of Saccharomyces, especially ESA1 mutants of S. cerevisiae.

It is a further purpose of this invention to provide methods for recombinant expression of the SAS2, SAS3, and ESA1 coding sequences. Hosts for recombinant expression include yeast, including Saccharomyces, cells.

This invention provides methods of isolating mutant strains of yeast based on their viability under certain conditions, particularly on their viability at certain temperatures, i.e. temperature sensitivity, or based on the presence or absence of reporter gene products and selectable markers well-known in the art.

This invention further provides for the mutant yeast strains, particularly strains of Saccharomyces, and more particularly S. cerevisiae, in which the mammalian homologues, including human homologues, of the yeast genes SAS2, SAS3, and/or ESA1 have been inserted. Human homologues include Tip60, MOZ, H11938, R96016, and Z25309. These strains are useful for screening agents to identify those effective in treating AIDS and AML.

The present invention further provides oligonucleotides, corresponding in sequence to at least 15 and up to 300 (contiguous) nucleotides of the specifically exemplified *S. cerevisiae* SAS2, SAS3, and EAS1 coding sequences, useful as probes, and primers, for detection or amplification of homologous sequences.

BRIEF DESCRIPTION OF THE DRAWINGS

FIG. 2 shows the protein alignment of *S. cerevisiae* Sas2p, *S. cerevisiae* Sas3p, *S. cerevisiae* Esa1p, *S. pombe* sas+, and human homologues Tip60 and Moz. Sas2p and related proteins share extensive similarity, and are homologous to known acetyltransferases. Identical and similar residues are highlighted. In cases where two residue pairs are found, Sas2p and Sas3p homologies are shown preferentially. Asterisks indicate the C2HC motif. Protein alignment was generated using the GCG Pileup program with standard options. The amino acid sequences of the SAS2, SAS3, ESA1, SpSAS+, TIP60 and MOZ proteins are given in SEQ ID NO:2(amino acids 23–338), SEQ ID NO:4(amino acids 222–579), SEQ ID NO:6(amino acids 151–440), and SEQ ID NO:23, 24 and 25, respectively, FIG. 3 shows the phenotypes (viability/growth and mating efficiency) for various mutant strains of *S. cerevisiae*, including strains with sir1, sas2, and sas3 mutations. Silencing of the HML locus was assayed by mating tests. Strains analyzed were (top to bottom): W303-1a, LPY6, LPY1382, LPY1590, LPY1381, LPY1591, LPY1592, and LPY1594. Although none of the single mutants had a significant mating defect, the sir1 sas3 double mutant mated slightly less well than wild type, the sir1 sas2 double mutant mated very weakly, and the sir1 sas2 sas3 triple mutant was nonmating.

DETAILED DESCRIPTION OF THE INVENTION

Figure 1:
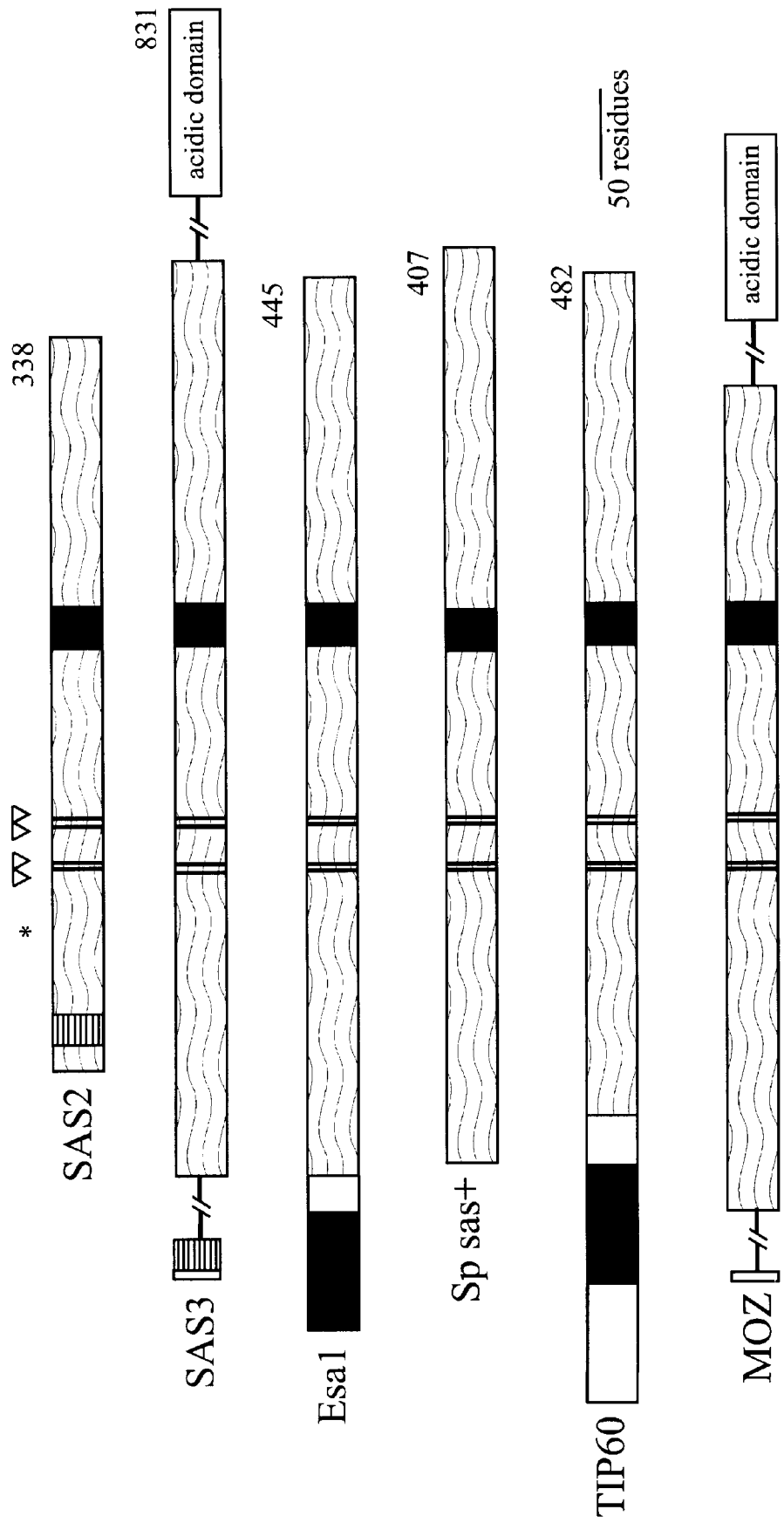
FIG. 1 is a schematic representation of *S. cerevisiae* Sas2p, *S. cerevisiae* Sas3p, the protein encoded by *S. cerevisiae* ESA1, *S. pombe* sas+, human Moz, and human Tip60, showing regions of sequence similarity. Esa1p, Sas2p and Sas3p are related to the human proteins MOZ is and Tip60, and *S. pombe* SAS3. Hatched areas denote regions of sequence similarity. The invariant Cys-Cys-His-Cys residues comprising a putative C2HC zinc finger motif are indicated by open arrowheads. The location of the sas2-92 lesion leading to truncation at amino acid 64 is indicated by an asterisk. Grey boxes indicate regions of similarity to acetyltransferases. Black boxes indicate a region of similarity shared only between Sas2p and Sas3p. Numbers refer to the total open reading frame length for each protein. Divergent regions are indicated by open boxes and for Sas3p (340 amino acids) and MOZ (350 and 345 amino acids) are abbreviated with break points. Noted regions of Sas3p and MOZ are similar in acidic nature, but not sequence.

Sir1p is not necessary for maintenance or propagation of silencing. When individual cells from a sir1 mutant population are examined for HML silencing, 80% of the cells are transcriptionally active, and 20% of the cells are silenced [Pillus, L. et al. (1989) *Cell* 59:637–647]. Both transcriptional states appear to be stable and heritable through many cell divisions, although infrequent changes in state are observed. Because silencing at HML can be maintained and propagated in the complete absence of Sir1p, it cannot be essential for these functions.

The unusual properties of sir mutants reveal an underlying epigenetic component of silencing in yeast: genetically identical cells can exist in phenotypically different transcriptional states. Switches between the two phenotypic states occur, but only rarely. These seemingly stochastic changes are believed to be a general feature of silencing. Telomere-proximal genes undergo comparable switches, and both active and silenced states are heritable [Gottschling, D. et al. (1990) *Cell* 63:751–762].

The existence of yeast cells that are silenced even in the presence of Sir1p prompted a search for novel enhancers of the sir1 mutant phenotype. To identify such enhancers, we searched for mutants defective in silencing at the silent mating-type (HM) loci if and only if Sirp1 were absent.

Yeast silencing defects most often result in complete derepression of telomere-proximal reporter genes and haploid sterility due to expression of the ordinarily repressed silent mating-type loci. In contrast, sir1 mutants have no apparent effect on telomeric silencing and in populations are mating-competent because, as noted above, 20% of the mutant population is silenced/repressed at the silent mating-type (HM) loci.

The unusual mutant sir1 phenotypes allowed us to identify silencing gene mutations that do not lead to complete loss of silencing [Reifsnyder, C. et al. (1996) *Nat. Genetics* 14:42–49]. We designed a screen for enhancers of the sir1 mutant phenotype (unable to mate). We sought mutants that were mating competent in the presence of the SIR1 gene, but that were mating defective in its absence. Such mutants are believed to have mutations in genes whose products can make a secondary contribution to silencing.

Mutant sir1 strains bearing a plasmid copy of the wild-type SIR1 gene, LPY94 and LPY122, were mutagenized to 50% survival using either ethyl methane sulfonate (EMS) or ultraviolet (UV) radiation. Mutagenesis was performed on 43 independent cultures, with more than 340,000 total colonies assayed. Colonies were selected both for the presence and absence of the SIR1 plasmid by replica plating to uracil drop out (medium containing all nutrients essential for growth except uracil) and 5-FOA (5-fluoroorotic acid) plates, respectively. These were then replica plated to a mating tester. Thirty-nine independent mutants in at least seven complementation groups were identified. Five of these complementation groups represented unusual alleles of genes that had previously been identified as silencing-related. A single mutant, eso1-1, represented a unique complementation group. eso candidates mated in the presence of the SIR1 plasmid, but were non-mating in its absence. Because eso1-1 behaved as a recessive allele, we were able to clone the ESO1 gene by complementation of the sir1 eso1-1 non-mating phenotype.

A MATa eso1-1 sir Δ:: URA3 strain (LPY998) was transformed with a LEU2-CENgenomic library. Approximately 13,000 transformants were tested for their ability to mate with a MATα strain. Fourteen plasmid-dependent mating-competent transformants were identified. Analysis of the plasmids revealed two classes of inserts: one expected class containing the SIR1 gene and a second class of insert which was different from SIR1. From the second class, a subcloned 3-kb HindIII fragment (pLP276) was capable of restoring mating when transformed into the MATa eso1-1 sir Δ::LEU2 mutant (LPY1000). This insert was radiolabelled and hybridized to the ordered array of yeast genomic λ phage clones [Olson, M. et al. (1986) Proc. Natl. Acad. Sci. USA 83:7826–7830; Link, A. et al. (1991) Genetics 127:681–698); Riles, L. (1993) Genetics 134:81–150]. A phage hybridizing to the cloned insert was localized to a position on the right arm of chromosome XIII near GCR3. We confirmed that the insert encoded the ESO1 structural gene through a series of crosses with eso1-1, an integrated deletion allele and mutant alleles of GCR3 and ILV2. These crosses placed the ESO1 locus 2 cM from GCR3 and 18 cM from ILV2.

Partial sequence of the pLP276 insert was compared to the GenBank data base. The ESO1 sequence was identical to that of the SAS2 gene. Several sas2 alleles were also identified in a screen for suppressors of a defective silencer element [Ehrenhofer-Murray, A. et al. (1997) Genetics 145:923–934]. Allelism tests between eso1-1 and known sas2 alleles confirmed that eso1-1 is an allele of SAS2, and that sas2 alleles can have an eso phenotype, e.g., enhanced mutant sir1 (sir one) mating defect—that is unable to mate in the absence of SIR1. Accordingly, eso1-1 was renamed sas2-92.

A BLAST (basic local alignment search technique protein) computer analysis of the complete 338 amino acid SAS2 sequence against both GenBank and the XREF data base revealed significant similarity to a previously annotated S. cerevisiae open reading frame (YBF2), an S. pombe open reading frame and to several human sequences. YBF2 was identified by the yeast genome sequencing project as a non-essential gene on the left arm of chromosome 11 [Scherens, B. et al. (1993) Yeast 9:1355–1371]. Because of its sequence similarities to SAS2 and mutant phenotypes, we renamed YBF2 SAS3.

Table 1 shows that the Sas2p, Sas3p and the protein encoded by S. cerevisiae ESA1 are each significantly homologous to the HIV-1 Tat interacting protein, Tip60, on human chromosome 11q13 [Kamine, J. et al. (1996) Virology 216:357–366] and to the 5' translocation partner of the Moz-CBP (Monocytic leukemia zinc finger protein-CREB binding protein) chimaeric oncogene product [Borrow, J. et al. (1996) Nature Genet. 14:33–41]. BLASTP comparisons resulting in the P values given for each pair suggest relative relatedness of the proteins. Percents identity and (similarity) are shown for pairwise comparisons of proteins. The 5' region of the translocation associated with this M4/M5 subtype of acute myeloid leukemia maps to the breakpoint on human chromosome 8p11. Several other sequences similar to Sas2p and Sas3p have also been obtained by XREF database analysis, indicating the existence in humans of a gene family of Sas-like proteins.

The term homologous as used herein refers to gene products which contain substantial similarity and/or identity with respect to the amino acid sequences. The % identity as used herein refers to the percentage of residues in the aligned proteins which were identical. The % similarity was calculated based on the following residues being considered similar: F (phenylalanine), I (isoleucine), L (leucine), V (valine), M (methionine), and A (alanine) were considered similar to each other; R (arginine) and K (lysine) were considered similar to each other; and D (aspartic acid), E (glutamic acid) and N (asparagine) were considered similar to each other. The % similar as used herein refers to the percentage of residues in the aligned proteins which were identical or similar. Identical residues were included in those considered similar.

FIG. 1 shows that the alignment of the five predicted yeast and human open reading frames show several interesting sequence features. Sas2p and Sas3p have a short region of strong N-terminal similarity not shared with the S. pombe or human open reading frames. Sas3p and Moz share extensive stretches of acidic residues in the C-terminal regions of the proteins. The protein encoded by ESA1 and Tip60 share additional N-terminus similarity. The protein encoded by ESA1 does not have a putative zinc finger. The translocation breakpoint of the MOZ 5' 8p11 partner occurs just beyond this acidic region. The hatched areas denote regions of sequence similarity. The invariant Cys-Cys-His-Cys residues comprising a putative C2CH zinc finger motif are indicated by open arrowheads. The location of the sas2-92 mutation resulting in truncation at amino acid 64 is indicated by an asterisk. Grey boxes indicate regions of similarity to acetyltransferases. Black boxes indicate the region of similarity shared only between Sas2p and Sas3p. The numbers at the C-terminal ends refer to the open reading frame length for each protein. Divergent regions are indicated by open boxes and for Sas3p (340 amino acids) and Moz (350 and 345 amino acids) are abbreviated with break points. All of the open reading frames have significant similarity over an approximately 300 amino acid region, beginning at position 23 in Sas2p. Within this region of homology is a completely conserved C2CH sequence consistent with an unusual zinc-finger motif.

FIG. 2 shows extended sequence alignments of the most conserved regions of the yeast and human ORFs illustrating the significance of the overall similarity. FIG. 2 shows the protein alignment of S. cerevisiae Sas2p, Sas3p, and the protein encoded by S. cerevisiae ESA1 (Esa1p); S. pombe sas+; and human homologues Tip60 and Moz. Identical and similar residues are highlighted. Similar residues are defined as above, in reference to Table 1. In cases where two residue pairs are found, Sas2p and Sas3p homologies are shown preferentially. Asterisks indicate the C2CH motif. Protein alignment was generated using the GCG Pileup program with standard options. Sas2p and Sas3p contain many identical and similar amino acid residues to the human proteins Tip60 and Moz.

Table 2 shows protein alignment of S. cerevisiae Sas2p, S. cerevisiae Sas3p, S. cerevisiae Esa1p, ESA1, S. pombe sas+, and human homologues Tip60 and Moz with several known acetyltransferases. Table 2 shows a subregion with striking similarity in Sas2p, Sas3p and the protein encoded by S. cerevisiae ESA1, and in diverse acetyltransferases, including histone acetyltransferases (Hat1p, TtHATA1 and human and yeast Gcn5p), prokaryotic ribosomal protein $N^\alpha$-acetyltransferases (RIMI and HEAHI), and essential (Nat2p) and non-essential yeast $N^\alpha$-acetyltransferases (Ard1p and Mak3p). The alignment begins 103 residues downstream of the first C of the C2CH motif noted for Sas2p (FIG. 1) and was constructed to highlight identical and conserved residues (shown in bold) without introducing gaps between the sequences under comparison. A salient feature of this alignment is the single, conserved glycine (underlined in Mak3p). Mutation of the MAK3 coding sequence for the GI pair results in loss of biological activity. Without wishing to be bound by any particular theory, the Sas2 and Sas3 proteins are concluded to have acetyltransferase activity, based on regions of these proteins with significant relatedness to portions of known acetyltransferases.

The phenotypes of the sas2-92 allele and null mutants of SAS2 and SAS3 were determined. Neither gene is essential for viability or mating. Both sas2 and sas3 mutants had distinct silencing phenotypes. FIG. 3 shows the phenotypes of silencing at the HML locus with various mutations.

Both a MATa sir1 sas2-92 strain and a MATa sir1 sas2 deletion strain (sas2Δ::TRP1, LPY1381) had severely reduced mating ability only in MATa strains (FIG. 3). No mating defect was seen in a MATα sir1 sas2-92 strain or a MATa sir1 sas2 deletion allele strain.

Loss of SAS2 function does not cause substantial derepression of the silent mating-type loci. Both MATa and MATα sas2Δ (null) strains mated as long as functional a Sir1p was present, although mating was decreased somewhat. Strains with sir1 sas2-92 and sir1 sas2Δ mutations had approximately 1,000-fold lower mating efficiency than wild-type.

Mutations in SAS3 caused less derepression of the HML locus than did mutations in SAS2. The strong HML derepression observed in sir1 sas2 strains was observed to a lesser extent in sir1 sas3 strains, as shown in FIG. 3. Sir1 sas3 double mutant strains had a mating efficiency of 0.16 compared to wild-type. Strains with a sas3 mutation alone or a mutation in both sas2 and sas3 mated as well as the wild-type. However, the sir1 sir2 sas3 triple mutant strain mated 30-fold more poorly than did the sir1 sas2 mutant.

There were no mating defects observed in MATα sas3 mutants or mutant combinations. Single or multiple mutations in SAS2 and/or combinations of mutations of SAS2 with SIR1 and SAS3 have no effect on mating in a type yeast cells.

Because other genes which act on the silent mating-type loci are often also active in repression of telomere-proximal reporter genes, SAS2 and SAS3 were evaluated for their activity in telomeric silencing. SAS2 and SAS3 were deleted in a strain (UCC1001) with URA3 integrated near the telomere of the left arm of chromosome VII. At this position, URA3 gene expression is variable in wild-type strains. Approximately 50% of these cells are transcriptionally active and 50% are silenced [Gottschling, E. et al. (1990) Cell 63: 751–762]. Expression of URA3 was evaluated by monitoring sensitivity to 5-fluoroorotic acid (5-FOA). In cells with transcriptionally active URA3, 5-FOA is a suicide substrate. Hence, the proportion of cells in a population resistant to 5-FOA is a measure of the number of silenced cells in the population [Gottschling, E. et al. (1990) Cell 63: 751–762].

Wild-type and sir1 mutants grew to intermediate levels on 5-FOA, as has previously been reported [Aparicio, O. et al. (1991) Cell 66: 1279–1287]. The sas3 mutants grew to a comparable level. The sir1 and sas3 mutants showed variable slight increases in 5-FOA resistance compared to wild-type. Total loss of silencing of the telomere-proximal gene URA3 was observed in sas2 and sir1 sas2 mutants, as evidenced by their complete sensitivity to 5-FOA. Because the sas2 mutant is as sensitive as the sir1 sas2 double mutant to 5-FOA, telomeric derepression appears to be the result of loss of SAS2 function.

The loss of telomeric silencing caused by sas2 mutations and loss of mating ability in the MATa sir1 sas2 strain suggested that SAS2 contributes to repression at telomere-proximal loci and silent mating-type loci. SAS2 appears to have a smaller effect on repression at these loci.

Multiple sas2 alleles have been recovered in a genetic screen to identify suppressors of HMRE site mutants [Ehrenhofer-Murray et al. (1997) supra]. This also indicated that SAS2 contributes to derepression at a mutated silencer. The wild-type HMRE silencer has three functional elements: 1) an autonomously replicating sequence (ARS) consensus site through which 2) the ORC binds, and 3) binding sites for the transcription factors Rap1p and Abf1p [Dillin, A. et al. (1995) Trends Biochem. Sci. 20:231–235]. The HMRE silencer contains substantial functional redundancy. Mutation of one element does not lead to loss of silencing; mutation of two or three elements leads to loss of silencing and a non-mating haploid phenotype [Brand, A. et al. (1987) Cell 51:709–719; Kimmerly, W. et al. (1988) EMBO J. 7:2241–2253].

Figure 5:
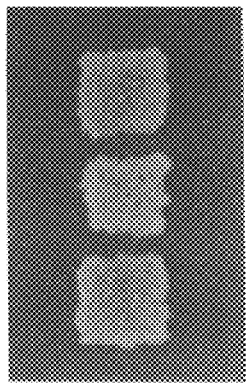
FIG. 5 shows the phenotype (viability/growth and mating efficiency) for various mutant strains of *S. cerevisiae*, all of which have mutations in the Rap1p and Abf1 binding sites at the HMRE locus, and some of which also have sir1, sas2, and sas3 mutations. sas2 and sas3 mutations suppressed the silencing defect of Hmra-e** in JRY2069, in which both the Rap1p and Abf1p binding sites are mutated. HMR silencing was assayed by mating tests. Results for the following strains are shown: JRY2069, DRY23, and LPY2137. Both mutant strains mate more efficiently than the JRY2069 parent.

The effects of mutant sas2 or sas3 alleles in a strain with mutations in the Rap1p and Abf1p binding sites at HMRE (JRY2069) were determined. This strain simultaneously expresses both α cell-type information from the MAT locus and a cell-type information from the mutated HMR locus [Axelrod, R. et al. (1991) Mol. Cell. Biol. 11:1080–1091]. FIG. 5 shows that mutation of either SAS2 or SAS3 led to significant restoration of mating relative to the parental control.

The phenotypic effects of sas2 and sas3 mutations at the mutated HMRa locus are opposite to the phenotypic effects of sas2 and sas3 mutations at the HMLα locus. SAS2 and SAS3 have similar functions at the HMRE locus.

The experiments disclosed herein illustrate that the closely related genes SAS2 and SAS3 both perform silencing functions and that these functions are distinct. Loss of SAS2, alone or in combination with sir1 mutations, led to loss of silencing at the HML locus and a telomere-proximal reporter gene. Loss of SAS3 had minimal effects at the HML locus and had no effect on silencing of telomere-proximal genes. Loss of either SAS2 or SAS3 restored silencing to a mutated HMRE locus.

The sequence similarity of SAS2 and SAS3 to known acetyltransferases prompted us to ask if there were also phenotypic similarities to acetyltransferase mutants. We focused our attention on NAT1 and ARD1, which encode sub-units of a non-essential N-terminal acetyltransferase activity. Both nat1 and ard1 mutations have documented effects on silencing: they interfere with telomeric silencing and act as eso mutants in MATa sir1 cells [Whiteway, M. et al. (1987) Mol. Cell. Biol. 7:3713–3722; Mullen J. R. et al (1989) *EMBO J.* 8:2067–2075; Lee, F.-J. S. et al. (1989), *J. Bacteriol.* 171:5795–5802; Aparicio, O. M. et al. (1991), *Cell* 66:1279–1287].

Additional phenotypes characteristic of abnormal cell cycle control have been noted, such as a failure to properly arrest in $G_0$ when limited for nutrients [Mullen J. R. et al. (1989) *EMBO J.* 8:2067–2075; Lee, F.-J. S. et al. (1989) *J. Bacteriol.* 171:5795–5802]. Wild-type yeast cells ordinarily arrest in $G_0$ when starved for nutrients and upon return to rich growth medium, have very high levels of viability.

Figure 6:
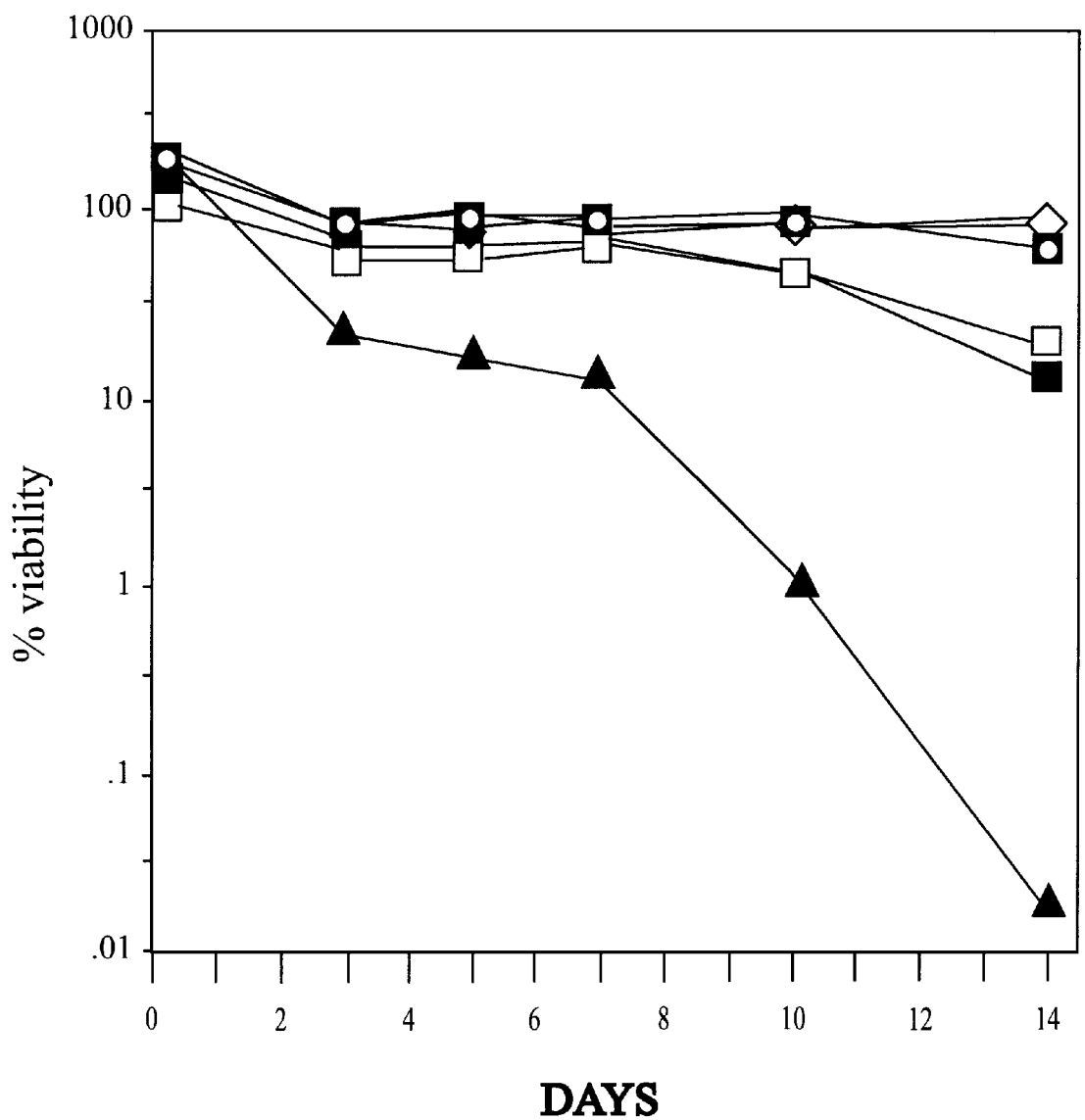
FIG. 6 is a graph of viability versus time, in days, for various mutant strains of *S. cerevisiae*, including strains with nat1, sas2, and sas3 mutations. The sas2nat1 mutant exhibits a stationary phase defect. Wild-type (W303-1a), sas2 (LPY1382), and sas3 (LPY1590), nat1 (AMR1), sas2nat1 (LPY1799), sas3nat1 (LPY1801), and sas2sas3 (LPY1592) strains were grown in liquid YPD at 30° C. and plated to assess viability after 4 h, and 1, 3, 5, 7, 10 and 14 days. The sas2 effect on viability was seen only in combination with nat1. The results shown are representative of three separate experiments performed with at least duplicate samples.

The sas2 and sas3 mutants were evaluated for their ability to achieve and maintain Go arrest. Their ability to survive extended periods with limited nutrients was tested. Cells were inoculated in rich medium, then after variable times, viability was tested. FIG. 6 shows that wild-type, sas2 and sas3 single mutants and the sas2 sas3 double mutant had high levels of viability, even after extended periods of nutrient limitation. The nat1 and nat1 sas3 mutants had comparable losses of viability that were particularly evident after greater than seven days in culture. The nat1 sas2 mutants showed earlier loss of viability and greater total loss of viability than any other mutant or mutant combination. Viability of the nat1 sas2 sas3 triple mutant was comparable to that of the nat1 sas2 mutant. The synergistic loss of viability observed in the nat1 sas2 double mutant suggested that SAS2 normally contributes to $G_0$ entry and/or stationary phase survival in nat1 mutants.

In the search for genes that enhance the epigenetic silencing defects of yeast sir1 mutants, we identified the related genes SAS2 and SAS3. Disruption of SAS2 or SAS3 also leads to silencing phenotypes in wild-type SIR1 strains, demonstrating independent silencing functions for these genes. Similar but distinguishable mutant phenotypes and significant sequence similarities suggest that SAS2 and SAS3 are functionally related. SAS2 and SAS3 are also related to a family of acetyltransferases and in particular, to newly identified human genes that are distinguished by their association with a recurrent translocation leading to acute myeloid leukemia [Borrow, J. et al. (1996) *Nature Genet.* 14:33–41] and with interaction with the HIV-1 Tat protein [Kamine, J. et al. (1996) *Virology* 216:357–366]. Taken together, these data point to conserved mechanisms for silencing transcription in yeast and humans.

Figure 4:
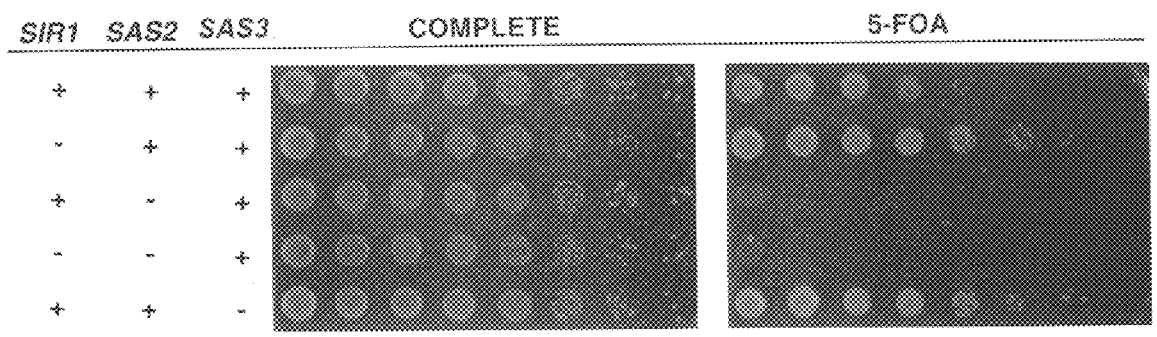
FIG. 4 shows the phenotypes (sensitivity to 5-FOA) for various mutant strains of S. cerevisiae, including strains with sir1, sas2, and sas3 mutations and a telomere proximal URA-3 gene. Serial dilutions of saturated cultures were replicated onto synthetic complete medium to evaluate growth or 5-FOA medium to evaluate expression of a telomere-proximal URA3 gene. Only those cells in which the telomeric reporter was repressed were able to grow in the presence of 5-FOA. Silencing was compared for the following strains (top to bottom): UCC1001, LPY1285, LPY2058, LPY2062, and LPY2121. The sas3 deletion strains were unable to silence the telomeric reporter.

SAS2 and SAS3 influence repression of silent mating-type information and SAS2 is essential for silencing telomere proximal genes. Some phenotypes of sas2 and sas3 mutants resemble phenotypes observed for nat1 and ard1 mutants. For example, derepression of HML, but not HMR, is observed in sas2, nat1 and ard1 mutants. The magnitude of derepression is increased significantly in the absence of Sir1p, and also reveals a contribution of SAS3 to HML silencing [Figure 3; Whiteway, M. et al. (1987) Mol. Cell. Biol. 7:3713–3722; Mullen J. et al. (1989) *EMBO J.* 8: 2067–2075; Lee, F. J. S. et al. (1989) *J. Bacteriol.* 171:5795–5802]. Likewise, telomeric silencing is abrogated in sas2, nat1 and ard1 mutants, but not in sas3 mutants [Figure 4; Aparicio, O. et al. (1991) *Cell* 66:1279–1287]. In contrast to these loss of silencing phenotypes at HML and telomeres, silencing is restored when SAS2 or SAS3 is disrupted in a strain with a mutated HMRE silencer. Thus, the genes appear to have potentially positive or negative influences on transcription, depending on the context of the locus examined. Different regions of the genome are believed to be differentially sensitive to the same silencing proteins [Renauld, H. et al. (1993) *Genes Dev.* 7:1133–1145; Kennedy, B. K. et al. (1995) *Cell* 80:485–496]. In this case, it is likely that Sas2p or Sas3p act on locus-specific substrates, or that different loci are differentially sensitive to the modification state of common targets.

Single nat1 and ard1 mutants fail to enter $G_0$ properly, are extremely heat shock sensitive in stationary phase and fail to sporulate when homozygous for either mutation. Because of the similarity of these phenotypes to those of several mutations in the cAMP pathway regulating nutrient response, it is believed that one or more of the proteins in this response pathway are targets for N-terminal acetylation [Mullen J. R. et al (1989) *EMBO J.* 8:2067–2075; Lee, F.-J. S. et al. (1989) *J. Bacteriol.* 171:5795–5802]. Loss of SAS2 or SAS3 function does not lead to similar phenotypes; that is, these mutants do not lose viability (FIG. 6) or suffer heat shock sensitivity in stationary phase, and do not fail to sporulate. However, the nat1 sas2 cells have a significantly greater loss of viability than the nat1 mutant alone, suggesting that SAS2 contributes to nat1 mutant stationary phase arrest and survival.

Localized sequence similarities between yeast Sas2p and Sas3p and the human Tip60 and MOZ genes are striking. In the most conserved regions, the proteins are predicted to be between 82% and 96% similar (Table 1). Completely conserved between the four proteins is a C2HC motif that is believed to exist as a single zinc finger with C—$X_2$—C—$X_{13}$—H—X—C spacing. C2HC motifs are less common than other zinc finger motifs, although they are found with shorter internal spacing in retroviral nucleocapsid proteins. Protein zinc fingers are believed to function in single- or double-stranded nucleic acid binding, and single fingers are believed to facilitate oligomerization or protein-protein interactions [Berg, J. M. et al. (1996) *Science* 271:1081–1085].

The amino acid similarities among SasZp, Sas3, Esa1p, Tip60 and Moz-CBP (see Table 2) are shared by broadly conserved proteins, many of which have been demonstrated to have acetyltransferase activities. Close relationships are observed with both histone acetyltransferases and N-terminal acetyltransferases. Similarities between acetyltransferases have been noted [Kleff, S. et al (1995) *J. Biol. Chem.* 270:24674–25677; Tercero, J. C. et al. (1992) *J. Biol. Chem.* 267:20277–20281]. Other recent alignments building on studies of chloramphenicol acetyltransferase [Shaw, W. V. et al. (1991) *Annu. Rev. Biophys. Chem.* 20:363–386] highlight H and C residues proposed to be involved in substrate binding and/or catalysis [Brownell, J. E. et al. (1996) *Curr. Opin. Genet. Dev.* 6:176–184). The alignments developed here (Table 2) emphasize different regions of conservation and do not highlight the same residues proposed to be involved in catalysis [Brownell, J. E. et al. (1996), *Curr. Opin. Genet. Dev.* 6:176–184].

Without wishing to be bound by any particular theory, it is believed that Sas2p, Sas3p, Esa1p, Moz and Tip60 are acetyltransferases, based on the sequence similarities and the yeast mutant phenotypes. An in vitro assay (Example 7 below) demonstrated that Esa1p has HAT (histone acetyltransferase) activity similar to that of Gcn5p, a previously demonstrated HAT [Brownell, J. E. et al. (1996) *Cell* 84:843–851]. If the other proteins have acetyltransferase activities, it will be useful to determine whether they function as NATs, or in gene activation like the HAT A proteins, including the Tetrahymena HAT protein and its yeast and human Gcn5p homologues [Brownell, J. E. et al. (1996) *Cell* 84:843–851; Candau, R. et al. (1996) *Mol. Cell. Biol.* 16:593–602] that have documented roles in transcriptional activation [Georgakopoulos, T. et al. (1992) *EMBO J.* 11:4145–4152; Marcus, G. et al. (1994) *EMBO J.* 13:4807–4815].

Overexpression of Tip60 results in modest increases of Tat transactivation of the HIV-1 promoter in transient expression assays [Kamine, J. et al. (1996) *Virology* 216:357–366], and although broadly expressed, its normal cellular functions are not yet known [Kamine, J. et al. (1996) *Virology* 216:357–366; Borrow, J. et al. (1996) *Nature Genet.* 14:33–41]. However, since the SAS2-like genes are also similar to a yeast HAT B enzyme (HAT1), they might instead function in chromatin assembly, as newly synthesized histones are acetylated and then deposited on DNA [Brownell, J. E. and Allis, C. D. (1996) *Curr. Opin. Genet. Dev.* 6:176–184]. Because there is no direct evidence for this activity, and hat1 mutants do not exhibit sas2 or sas3 phenotypes [Kleff, S. et al. (1995) *J. Biol. Chem.* 270:24674–25677); Parthunm M. et al. (1996) *Cell* 87:85–94], it is believed that SAS2, SAS3 and their homologues have protein acetylation activities on substrates other than or in addition to histones or histone proteins.

The present disclosure of the silencing genes SAS2 and SAS3 and their *S. pombe* and human homologues provides key evidence for the existence of conserved mechanisms important for silencing. The telomeric and silent mating-type phenotypes of sas2 and sas3 mutants suggest that components of silenced chromatin are sensitive to their function. Because loss of SAS function can either interfere with, or restore, silencing depending on the locus examined, it is likely that there is more than one target for SAS2 or SAS3 activity. The specific target(s) that contribute to silencing defects or the lethality observed in the nat1 sas2 mutant is not known. The $G_0$ arrest defects and recent experiments suggesting that distinct silenced loci are important for lifespan control [Kennedy, B. K. et al. (1995) *Cell* 80:485–496] are relevant to pathologies associated with HIV-1 infection and the Moz-CBP chimeric protein. In either case, abrogation of normal silencing contributes to loss of cell cycle control and reprogramming of transcriptional activities. The structure of the Moz-CBP oncoprotein is particularly telling [Borrow, J. et al. (1996) *Nature Genet.* 14:33–41]. Its central domain consists of the regions of greatest similarity to the yeast proteins and the proposed acetyltransferase domain. The breakpoint fusion leaves much of CBP intact, including the CREB binding domain and the bromodomain [Borrow, J. et al. (1996) *Nature Genet.* 14:33–41; Chrivia, J. C. et al. (1993) *Nature* 365:855–859]. The structure of the leukemia-associated fusion protein is extremely evocative of domains described for the HAT A proteins: a conserved acetyltransferase domain and a C-terminal bromodomain [Brownell, J. E. et al. (1996) *Cell* 84:843–851]. Because the HAT As are directly involved in transcriptional activation through histone acetylation and are physically associated with chromatin [Brownell, J. E. et al. (1996) *Cell* 84:843–851; Brownell, J. E. et al. (1996) *Curr. Opin. Genet. Dev.* 6:176–184; Brownell, J. E. et al. (1995) *Proc. Natl. Acad. Sci. USA* 92:6364–6368] we believe that the MOZ-CBP chimaera acts as a dominant-negative regulator of chromatin structure and transcriptional regulation. Determining the targets of this abnormal regulation will be key to understanding failure of monocyte differentiation associated with the t(8;16)(p11;13) translocation [Hanslip, J. I. et al. (1992) *Leuk. Lymph.* 6:479–486].

Sas2p and Sas3p appear more closely related to their respective human homologues than to each other (Table 1). The sequence relationships observed are evocative of those in the recently discovered HST Homologues of SIR62) gene family [Brachmann, C. B. et al. (1995) *Genes Dev.* 9:2888–2902], where some of the yeast homologues are more closely related to human genes than they are to other yeast genes. Future studies should distinguish the functional relationships between the SAS-like proteins.

SAS2 and SAS3 join the growing list of yeast genes with human-disease associations. For example, the related genes TEL1 and MEC1 have sequence and phenotypic similarities to the gene mutated in patients with Ataxia telangiectasia [Savitsky, K. et al. (1995) *Science* 268:1749–1753; Greenwell, P. W. et al. (1995) *Cell* 82:823–829; Morrow, D. W. et al. (1995) *Cell* 82:831–840]. Pairs of yeast genes have also been described that are similar to genes mutated in neurofibromatosis type 1, X-linked adrenoleukodystrophy and hereditary nonpolyposis colon cancer [Bassett, D. E. et al. (1996) *Nature* 379:589–590]. Genetic and biochemical studies of SAS2 and SAS3 functions provide better understanding of altered transcriptional control in HIV-1 infected cells and monocytic development that is disrupted in AML.

A third gene, ESA1, was discovered by comparing the sequences of SAS2 and SAS3 to the *S. cerevisiae* genome data in the Saccharomyces Genome Database (http://genome-www.stanford.edu/saccharomyces/SacchDB4.6.1). ESA1 has been cloned using sequence information. A probe was generated by PCR and then a library was screened.

U.S. Pat. No. 4,683,195 and U.S. Pat. No. 4,683,202, both to Kary Mullis, and both of which are specifically incorporated in their entirety by reference herein, describe the use of primers, probes and PCR. A primer is an oligonucleotide, either occurring naturally, purified from a restriction endonuclease digest or produced synthetically, which is capable of acting as a point of initiation of synthesis when placed under conditions in which synthesis of a primer extension product which is complementary to a nucleic acid strand is induced, i.e., in the presence of nucleotides and a polymerization reagent such as DNA polymerase and at a suitable temperature and pH. A probe is the nucleic acid complement of a specific nucleic acid sequence.

Table 1 shows that the protein encoded by ESA1 (Esa1p) has even greater homology to the human gene products, Tip60 and Moz, than do Sas2p and Sas3p. The nucleic acid sequence for ESA1 is given in SEQ ID NO:5. Without wishing to be bound by any particular theory, the protein encoded by ESA1 has acetyltransferase activity, based on regions with significant relatedness to portions of known acetyltransferases and based on data described in Example 7 below. Because the entire *S. cerevisiae* genome has been sequenced and no additional homologues were uncovered, we believe that SAS2, SAS3 and ESA1 are the only members of this family of genes in *S. cerevisiae*.

The activity of ESA1 is believed necessary for expression of an essential yeast gene. An in vitro assay (Example 7 below) demonstrated that ESA1 has HAT (histone acetyltransferase) activity similar to that of Gcn5p, a previously demonstrated HAT [Brownell, J. E. et al. (1996) *Cell* 84:843–851]. Unlike SAS2 and SAS3, ESA1 is an essential gene. Null mutations in ESA1 lead to cell death.

Strains with temperature sensitive ESA1 mutations have decreased viability at approximately 30° to 33° C. and die at approximately 34° to 36° C. Wild-type *S. cerevisiae* is viable at temperatures ranging from 4° to 37° C. In the laboratory, *S. cerevisiae* are generally maintained at approximately 25° to 30° C. A temperature sensitive mutant as used herein refers to a mutant with a lower maximal temperature at which a strain is viable as compared to the wild type. At a permissive temperature (e.g., 25° C.) both temperature sensitive mutant and wild type grow, but at a restrictive temperature (e.g., 37° C.) only the wild type grows. Temperature sensitive alleles are useful as tools to assess protein function and identify interactions.

The differential temperature sensitivity of mutant ESA1 strains provides a convenient method to assay for agents which affect the expression of ESA1 or the activity of its gene product.

The present invention provides methods for screening agents for their ability to affect expression of genes at telomere-proximal loci and silent-mating type loci. The methods of this invention utilize the genes SAS2, SAS3 and ESA1 to screen the effect of various agents on gene expression at telomere-proximal loci and silent-mating type loci. Agents which affect expression of genes at telomere-proximal loci and silent-mating type loci exert their effects, at least in part, by affecting the activities of one or more of the gene products of SAS2, SAS3 and ESA1. Because of the homology among the silencers/genes SAS2, SAS3, ESA1 and the human genes TIP60 and MOZ, agents which affect expression of genes at telomere-proximal loci and silent mating-type loci, also affect the gene products of TIP60 and MOZ. Hence, the methods for screening agents for their ability to affect the TIP60 and MOZ gene products allow identification of agents which are effective in the treatment of AIDS and/or acute myeloid leukemia. The methods of this invention provide easy and inexpensive ways to screen agents, including but not limited to, naturally occurring, synthetic and/or semi-synthetic drug or small molecule libraries, to identify compounds which may become candidates for more expensive animal model or clinical tests.

SAS2 affects silencing of both telomere-proximal genes and silent mating-type genes. Assays for SAS2 activity can therefore utilize both telomere-proximal genes and silent mating-type genes or genes integrated at these loci.

One embodiment of the methods of this invention comprises assays for SAS2 and SAS3 activity which utilize a reporter gene, wherein the reporter gene is integrated into a silent mating-type locus and assays for SAS2 activity wherein the reporter gene is integrated into either a silent mating-type locus or a telomere-proximal locus, as exemplified above in the experiment with URA3. In the URA3 example provided herein, the URA3 gene in the silencing locus (telomere proximal or mating type locus such as HMRE) serves as a negative selection marker. That is, only when URA3 is not expressed (is silenced), can the cells grow in the presence of 5-FOA. A reporter gene is a gene which is operably linked to a regulatory region or sequence of interest, wherein the product of the reporter gene provides a detectable activity, preferably a quantifiable activity, including but not limited to, mating efficiency and cell viability. A selectable marker is a specialized type of reporter gene. Examples of reporter genes include, but are not limited to, chloramphenicol acetyltransferase and β-glucuronidase, which are useful in mammalian cells. The assays of this invention used selectable marker reporter genes which are biosynthetic genes e.g. TRP1 and ADE2, which complement a corresponding auxotrophic marker at the normal chromosomal locus. For example, expression of the selectable TRP1 marker allows the otherwise tryptophan-requiring cell to grow on minimal medium without added tryptophan. Compounds which modulate the activity of Sas2p or Sas3p or Esa1p similarly modulate the activity of human homologues Moz, Moz-CBP and Tip60.

A method for screening agents which affect the activity of Sas2p or the human proteins Tip60 and Moz-CBP includes the steps of:

a) exposing a mutant yeast strain containing a sas2 mutation and a reporter gene integrated into either a silent mating-type locus or a telomere-proximal locus, to the agent;

b) measuring an activity of the reporter gene product in the presence and absence of the agent;

c) exposing a wild-type strain containing a reporter gene integrated into either a silent mating-type locus or a telomere-proximal locus, to the agent and measuring an activity of the reporter gene product in the presence and absence of the agent; and d) comparing said activity of the mutant strain to the activity of a wild-type strain in the presence and absence of the agent, whereby an agent which affects the activity of Sas2p or Tip60 or Moz-CBP proteins is identified when the activities measured in steps (b) or (c) are significantly different.

An example of this method was described above in the experiment in which URA3 was integrated near the telomere of the left arm of chromosome VII and URA3 transcription was monitored by determining the level of 5-FOA sensitivity in a population of cells with various mutations. Because 5-FOA is a suicide substrate for cells expressing URA3, the proportion of cells in a population resistant to 5-FOA accurately reflects the number of silenced cells in the population. In this example the detectable activity is cell viability. Only those cells in which the telomeric reporter was repressed were able to grow in the presence of 5-FOA. Strains with sir1 and sas3 mutations showed variable, slight increases in 5-FOA resistance when compared to wild-type cells. The sas2 strains were unable to silence the telomeric reporter as evidenced by their lack of viability in the presence of 5-FOA.

As summarized above, loss of SAS2, alone or in combination with sir1 mutations, led to loss of silencing at the HML locus and a telomere-proximal reporter gene, and restored silencing at a mutated HMRE locus. However, loss of SAS3 had effects at the HML locus and restored silencing at a mutated HMRE locus, but no effect on silencing of telomere-proximal genes.

Therefore, this invention further provides a method for screening agents which affect the activity of Sas3p or Tip60 or Moz-CBP proteins and includes the steps of:

a) exposing a mutant yeast strain containing a sas3 mutation and a reporter gene integrated in a silent mating-type locus, to the agent;

b) measuring an activity known to be a result of the reporter gene product in the presence and absence of the agent;

c) exposing a wild-type strain containing a reporter gene integrated into a silent mating-type locus, to the agent measuring an activity of the reporter gene product in the presence and absence of the agent; and d) comparing said activity of the mutant strain to the activity of a wild-type strain, whereby an agent which affects the activity of Sas3p or Tip60 or Moz-CBP proteins is identified when the activities measured in steps in (b) or (c) are significantly different.

Another embodiment of the methods of this invention comprises assays for SAS2 and SAS3 activity which utilize a selectable marker. The term selectable marker as used herein refers to a particular type of reporter gene. Selectable markers can be used such that the cells will be able to grow only if expression of the selectable marker occurs.

An example of the use of a selectable marker to assay for SAS2 and SAS3 activity is the following. A wild-type TRP1 gene was integrated into the silent mating-type locus of a S. cerevisiae strain, and the normal chromosomal TRP1 locus contains a null allele of this tryptophan biosynthetic enzyme. The cells are plated in tryptophan-deficient medium. If the TRP1 gene is silenced (via SAS2 and/or SAS3 activity), then the yeast cells cannot grow in the absence of tryptophan. If the TRP1 is not silenced (because of sas2 and/or sas3 mutations), then the cells produce tryptophan and survive. A method for screening agents which affect SAS2 and SAS3 activity comprises monitoring mutant cells containing a selectable marker upon exposure to an agent and determining whether the mutant cells are able to survive more readily or whether the mutant cells are less viable under a given set of conditions, compared to wild-type cells.

Alternatively, an antibiotic resistance marker (e.g., the Tn5 npt gene) can be used as the selectable marker and growth in the presence and absence of the selective agent (antibiotic, e.g., G418 or kanamycin) can be determined.

A method for screening agents which affect the activity of Sas2p or Tip60 or Moz-CBP proteins includes the steps of:
a) exposing a mutant yeast strain containing a sas2 mutation and a selectable marker integrated into either a silent mating-type locus or a telomere-proximal locus, to the agent;
b) measuring an activity known to be a result of the selectable marker (usually detected via viability under selective conditions in the present and absence of the agent);
c) exposing a wild-type strain containing a selectable marker integrated into either a silent mating-type locus or a telomere-proximal locus to the agent measuring an activity of the reporter gene product in the presence and absence of the agent; and
d) comparing said activity of said mutant strain to the activity of a wild-type strain in the presence and absence of the agent, whereby an agent which affects the activity of Sas2p or Tip60 or Moz-CBP proteins is identified when the activities measured in steps (b) or (c) are significantly different.

This invention further provides a method for screening agents which affect the activity of Sas3p or Tip60 or Moz-CBP proteins including the steps of:
a) exposing a mutant yeast strain containing a sas3 mutation and a selectable marker integrated in a silent mating-type locus, to the agent;
b) measuring an activity known to be a result of the selectable marker in the presence and absence of the agent;
c) exposing a wild-type strain containing a selectable marker integrated into a silent mating-type locus to the agent and measuring an activity of the reporter gene product in the presence and absence of the agent; and
d) comparing the activity of said mutal strain to the activity of a wild-type strain in the present and absence of the agent, whereby an agent which affects the activity of Sas3p or Tip60 or Moz-CBP is identified when the activities measured in steps (b) or (c) are significantly different.

This invention further provides a method for screening agents which affect the activity of Esa1p or Tip60 or Moz-CBP proteins including the steps of:
a) exposing a mutant yeast strain containing a ESA1 mutation to various temperatures, and to the agent;
b) measuring temperature sensitivity of the mutant strain in the presence and absence of the agent;
c) exposing a wild-type strain to various temperatures and to the agent and measuring temperature sensitivity of the wild-type strain in the presence and absence of the agent; and
d) comparing the temperature sensitivity of the mutant strain to the temperature sensitivity of a wild-type strain in the presence and absence of the agent, whereby an agent which affects the activity of Esa1p or Tip60 or Moz-CBP proteins is identified when the activities measured in steps (b) and/or (c) are significantly different.

The specific coding sequences disclosed herein, SAS2, SAS3, and ESA1, are from *S. cerevisiae*. It will be understood by those of ordinary skill in the art that homologous genes occur in the genomes of other species of Saccharomyces, e.g. *S. uvarum*, and other genera of yeast, e.g. Schizosaccharomyces (*S. pombe*) and Candida (*C. albicans*), as well as in other eukaryotes, e.g. Caenorhabditis (*C. elegans*), Arabidopsis (*A. thaliana*) and humans (*Homo sapiens*). Specific examples are *S. pombe* SAS and the five human coding sequences, TIP60 [Kamine, J. et al. (1996) *Virology* 216:357–366]; MOZ [Borrow, J. et al. (1996) *Nature Genet.* 14:33–41]; Z25309 (sequence is found in GenBank under this listing); and H11938 (sequence is found in GenBank under this listing). TIP60, MOZ, R96016, Z25309 and H11938 are herein referred to as mammalian homologues of ESA1, specifically they are human homologues. Therefore the genes and methods of this invention include the homologous genes in organisms other than *S. cerevisiae*. Methods can be employed to isolate various mutant strains of yeast, including strains of Saccharomyces, useful in the methods of this invention [Sambrook et al. (1989) *Molecular Cloning*, second edition, Cold Spring Harbor Laboratory, Plainview, N.Y.].

Mammalian, and specifically human, homologues of ESA1 can be identified by heterologous complementation of a null *S. cerevisiae* EAS1 allele (cross-complementation). Mammalian, e.g., human, homologues of ESA1 can be used in yeast vectors to screen for agents which affect such homologues. Human homologues include without limitation TIP60, MOZ, R96016, Z25309 and H1 1938.

It will further be understood by those skilled in the art that other nucleic acid sequences besides those disclosed herein for SAS2, SAS3, and ESA1 will function as coding sequences synonymous with the exemplified coding sequences. Nucleic acid sequences are synonymous if the amino acid sequences encoded by those nucleic acid sequences are the same. The degeneracy of the genetic code is well known to the art. For many amino acids, there is more than one nucleotide triplet which serves as the codon for a particular amino acid, and one of ordinary skill in the art understands nucleotide or codon substitutions which do not affect the amino acid(s) encoded.

Specifically included in this invention are sequences from other strains of Saccharomyces and from other yeasts which hybridize to the sequences disclosed for SAS2, SAS3, and ESA1 under stringent conditions. Stringent conditions refer to conditions understood in the art for a given probe length and nucleotide composition and capable of hybridizing under stringent conditions means annealing to a subject nucleotide sequence, or its complementary strand, under standard conditions (i.e., high temperature and/or low salt content) which tend to disfavor annealing of unrelated sequences, (indicating about 50–100% nucleotide sequence identity). Also specifically included in this invention are sequences from other strains of Saccharomyces, other yeasts and other organisms, including but not limited to, humans, which hybridize to the sequences disclosed for SAS2, SAS3, and ESA1 under low stringency conditions. Low stringency conditions refer to conditions understood in the art for a given probe sequence and as used herein and in the claims, "conditions of low stringency" means hybridization and wash conditions of relatively low temperature and relatively high salt, 40°–50° C., 6× SSC and 0.1% SDS (indicating about 50–80% similarity, i.e. nucleotide sequence identity). Also specifically included in this invention are sequences from other strains of Saccharomyces and other yeasts which hybridize to the sequences disclosed for SAS2, SAS3, and ESA1 under moderately stringent conditions. Moderately stringent conditions refer to conditions understood in the art for a given probe sequence and "conditions of medium stringency" means hybridization and wash conditions of 50°–65 ° C., 1× SSC and 0.1% SDS (indicating about 80–95% similarity). Also specifically included in this invention are sequences from other strains of Saccharomyces, from other yeasts, and from other organisms, including humans, which hybridize to the sequences disclosed for SAS2, SAS3, and ESA1 under highly stringent conditions.

Highly stringent conditions refer to conditions understood in the art for a given probe sequence and "conditions of high stringency" means hybridization and wash conditions of 65°–68° C., 0.1× SSC and 0.1% SDS (indicating about 95–100% similarity). Hybridization assays and conditions are further described in Sambrook et al. (1989) supra.

A method for identifying other nucleic acids having silencing activity is also provided wherein nucleic acid molecules encoding silencing proteins are isolated from an organism and nucleic acid hybridization is performed with the nucleic acid molecules and a labeled probe having a nucleotide sequence that includes all or part of nucleotide sequence SEQ ID NO:1, 3, or 5. By this method, silencing genes similar to the SAS2, SAS3, or ESA1 genes may be identified and isolated from other yeasts or other organisms. All or part of a nucleotide sequence refers specifically to all continuous nucleotides of a nucleotide sequence, or e.g. 1000 continuous nucleotides, 500 continuous nucleotides, 100 continuous nucleotides, 25 continuous nucleotides, and 15 continuous nucleotides.

Sequences included in this invention are those amino acid sequences which are 20% similar to the amino acid sequences encoded by SAS2, SAS3, and ESA1. Sequences included in this invention are those amino acid sequences which are 35% similar to the amino acid sequences encoded by SAS2, SAS3, and ESA1. Sequences included in this invention are those amino acid sequences which are 50% similar to the amino acid sequences encoded by SAS2, SAS3, and ESA1. Sequences included in this invention are those amino acid sequences which are 75% similar to the amino acid sequences encoded by SAS2, SAS3, and ESA1. Sequences included in this invention are those amino acid sequences which are 90% similar to the amino acid sequences encoded by SAS2, SAS3, and ESA1. Probes for identifying homologous sequences are preferably designed using nucleotide sequences of the specifically exemplified yeast SAS2, SAS3 and/or ESA1 genes which correspond to conserved regions of the encoded proteins.

It is well-known in the biological arts that certain amino acid substitutions may be made in protein sequences without affecting the function of the protein. Generally, conservative amino acid substitutions or substitutions of similar amino acids are tolerated without affecting protein function. Similar amino acids can be those that are similar in size and/or charge properties, for example, aspartate and glutamate, and isoleucine and valine, are both pairs of similar amino acids. Similarity between amino acid pairs has been assessed in the art in a number of ways. For example, Dayhoff et al. (1978) in Atlas of Protein Sequence and Structure, Volume 5, Supplement 3, Chapter 22, pp. 345–352, which is incorporated by reference herein provides frequency tables for amino acid substitutions which can be employed as a measure of amino acid similarity.

Dayhoff et al. 's frequency tables are based on comparisons of amino acid sequences for proteins having the same function from a variety of evolutionarily different sources.

The following Examples, provided for illustrative purposes, are not intended to limit the scope of the invention. Those of ordinary skill in the art understand that variations, modifications, and adaptations in specific techniques, procedures, and methods can be made without departing from the spirit and scope of this invention. All such variations, modifications, and adaptations are encompassed by this invention.

The examples use many techniques well known and accessible to those skilled in the arts of molecular biology, in the manipulation of recombinant DNA in yeast and in the culture of yeast. Reagents, buffers, and culture conditions are also known to the art. References providing standard molecular biological procedures include Sambrook et al. (1989) *Molecular Cloning*, second edition, Cold Spring Harbor Laboratory, Plainview, N.Y.; Wu, R. (ed.) (1993) *Methods in Enzymology* 218; Wu et al. (eds.) *Methods in Enzymology* 100, 101; Guthrie and Fink (eds.) *Methods in Enzymology*, 194; Glover (ed.) (1985) *DNA Cloning*, Vols. I and II, IRL Press, Oxford, UK; Hames and Higgins (eds.) (1985) *Nucleic Acid Hybridization*, IRL Press, Oxford, UK. Abbreviations and nomenclature, where employed, are deemed standard in the field and are commonly used in professional journals such as those cited herein.

All references cited in the present application are expressly incorporated in their entirety by reference herein.

EXAMPLES

Example 1

Yeast Strains, Media, and Genetic Methods

Yeast strains used in this study were as follows: LPY2879:Mata his3Δ200 leu2-3,112 trp1Δ1 ura3-52 ESA1 Δ::HIS3 transformed with a plasmid bearing ESA1 [I368V] [L394Q]; LPY2889:Mata his3Δ200 leu2-3,112 trp1Δ1 ura3-52 ESA1 Δ::HIS3 transformed with a plasmid bearing ESA1 [S375P][S378P]; LPY2877:Mata his3Δ200 leu2-3,112 trp1Δ1 ura3-52 ESA1 Δ: :HIS3 transformed with a plasmid bearing ESA1 [S2P][L327P]; LPY6: MATa ade2-1 can1-1OO his3-11,15 leu2-3, 112 sir1Δ:.LEU2 trp1-1 ura3-1; LPY78: MAT αhis4; LPY94: MATa ade2-1 can1-100 his3-11,15 leu2-3,112 sir1Δ::LEU2 trp1-1 ura3-1, with pLP17; LPY122: MATα ade2-1 can1-100 his3-11,15leu2-3,112 sir1Δ::URA3 trp1-1 ura3-1, with pLP17; LPY142:MATa his4; LPY998: MATa ade2-1 can1-100 his3-11,15 leu2-3, 112 sir1Δ::URA3 trp1-1 ura3-1; LPY1000: MATa ade2-1 can1-100 his3-11,15 leu2-3,112 sas2-92 sir1Δ::LEU2 trp1-1 ura3-1; LPY1310: MATa ade2-101 his3-Δ200 leu2-Δ1 lys2-801 sas2Δ::TRP1 trp1-Δ1 ura3-52; LPY1312: MATa ade2-101 his3-Δ200 leu2-Δ1 lys2-801 sas2Δ::TRP1 trp1-Δ1 ura3-52 TELadh4::URA3; LPY1378: MATα ade2-1 can1-100 his3-11,15 leu2-3,112 sas2Δ::TRP1 sir1Δ::LEU2 trp1-1 ura3-1; LPY1379; MATα ade2-1 can1-100 his3-11, 15 leu2-3,112 sas2Δ::TRP1 trp1-1 ura3-1; LPY1381: MATa ade2-1 can1-100 his3-11,15 leu2-3,112 sas2Δ::TRP1 sir1Δ::LEU2 trp1-1 ura3-1; LPY1382; MATa ade2-1 can1-100 his3-11,15 leu2-3,112 sas2Δ::TRP1 trp1-1 ura3-1; LPY1592:MATa ade2-1 can1-100 his3-11,15 leu2-3,112 sas2Δ::TRP1 trp1-1 ura3-1 sas3Δ::URA3; LPY1619: MATa gcr3::URA3 ilv2 leu2 trp1 ura3; LPY 1799: MATa ade2-1 can1-100 his3-11,15 leu2-3,112 nat1Δ::LEU2 sas2Δ::TRP1 trp1-1 ura3-1; LPY1801: MATa ade2-1 can1-100 his3-11,15 leu2-3,112 nat1Δ::LEU2 trp1-1 ura3-1 sas3Δ::URA3; LPY1803: MATa ade2-1 can1-100 his3-11,15 leu2-3,112 nat1Δ::LEU2 sas2Δ::TRP1 trp1-1 ura3-1 sas3Δ::URA3;

LPY1590: MATa ade2-1 can1-100 his3-11, 15 leu2-3, 112 trp1-1 ura3-1 sas3Δ::URA3; LPY1285: MATa ade2-101 his3-66 200 leu2-Δ1 lys2-801 sir1Δ::HIS3 trp1-Δ ura3-52 TELadh4::URA3; LPY2058: MATa ade2-101 his3-Δ200 leu2-Δ1 lys2-801 sas2Δ::TRP1 trp1-Δ1 ura3-52 TELadh4::URA3; LPY2062: MATa ade2-101 his3-Δ200 leu2-Δ1 lys2-801 sas2Δ::TRP1 sir1Δ::HIS3trp1-Δ1 ura3-52 TELadh4::URA3; W3031a: MATa ade2-1 can1-100 his3-11,15leu2-3,112 trp1-1 ura3-1 (R. Rothstein); AMR1: MATa ade2-1 can1-100 his3-11,15 leu2-3,112 nat1Δ::LEU2 trp1-1 ura3-1 (R. Sternglanz); YPH250: MATa ade2-101 his3-Δ200 leu2-Δ1 lys2-801 trp1-Δ1 ura3-52 (D. Gottschling); UCC1001: MATa ade2-101 his 3-Δ200 leu2-Δ1 lys2-801 trp1-Δ1 ura3-52 TELadh4::URA3 (D. Gottschling); UCC1003: MATa ade2-101 his3-Δ200 leu2-Δ1 lys2-801 trp1-Δ1 ura3-52 adh4::URA3 (D. Gottschling); JRY2069: MATα HMRa-3 ade2-101 his3 lys2 tyr1 ura3-52 (J. Rine); DRY23: MATα HMRa-e ade2-101 his3 lys2 sas2-1 tyr1 ura3-52 (D. Rivier). Media and standard yeast manipulations were as described [Rose, M. D. et al. (1990), in *Methods in Yeast Genetics*, (Cold Spring Harbor Laboratory Press, Cold Spring Harbor, N.Y.)]. Mating assays [Sprague, G. F. (1991) *Meth. Enzym.* 194:77–93] and telomeric silencing assays [Gottschling, D. E. et al. (1990) *Cell* 63:751–762] were performed essentially as described, with the exception that strains were grown in liquid culture prior to testing telomeric silencing rather than on solid medium.

Example 2

SAS2 Screen

Thirty-five independent cultures of LPY94 and 8 independent cultures of LPY122 were mutagenized to 50% viability with either ultraviolet irradiation or the chemical mutagen ethyl methane sulfonate(Lawrence, C. W. (1991) then plated for single colonies onto uracil minus plates to maintain the SIR1-bearing plasmid, pLP17 (SIR1 in pRS316, a URA3-CEN vector). After 2–3 d, these were replica plated onto both uracil minus plates, to select for pSIR1, and 5-fluoro-orotic acid (5-FOA) plates to select for loss of pSIR1. After 1–3 d, these were replica mated to either LPY78 or LPY142. Colonies were picked that were able to mate when pSIR1 was maintained, but not when pSIR1 was lost.

Example 3

Cloning and Mapping SAS2

SAS2 was cloned by plasmid-based complementation of the SAS2 mating defect using a centromeric yeast genomic library [Spencer, F. et al. (1990) *Genetics* 124:237–249]. 13,000 LPY998 (MATa sir1Δ::URA3 sas2-92) transformants were tested for mating ability. Plasmids that restored mating were recovered from yeast and transformed into *E. coli* by standard techniques. Of these, $^{12}/_{14}$ contained SIR1; the remaining two plasmids contained identical inserts that were analyzed further.

The region of rescuing activity was localized to phage clone 70186 on the Olson mapping grid, a clone that maps physically to the right arm of chromosome XIII. Sequence from the rescuing fragment was compared to the GenBank database. This comparison demonstrated that the rescuing fragment contained the full coding sequence of SAS2. Other sequence analyses were performed using preset options of the BLASTP and Pileup programs.

The genetic map position for SAS2 was determined by a three factor cross between LPY1379 (sas2Δ::TRP1 GCR3 ILV2) and LPY1619 (ESO1 gcr3::URA3 ilv2). Fifty tetrads were examined, placing SAS2 2 cM from GCR3 and 18 cM from ILV2, located between the two genes.

Example 4

Identification of the sas2-92 Lesion and Construction of sas2 and sas3 Null Alleles We recovered the sas2-92 allele by standard gap-repair technology [Orr, W. T. et al. (1988) *Mol. Cell Biol.* 8:5292–5298]. Sequencing the relevant region of the gene in two independently repaired plasmids revealed a G to A mutation at base 1040 that would result in truncation of the open reading frame after amino acid 64. Two other lesions were also detected in this region when sequence was compared to the unmutagenized SAS2 locus: an A to G mutation at base 864 that would result in glycine substitution for the normally encoded serine, and a silent A to G mutation at position 971.

The sas2Δ::TRP1 construct (PDR369) was kindly provided by D. Rivier. A 653-bp BglII-StuI fragment was removed from pDR44 (3-kb HindIII SAS2 fragment in the LEU2-CEN library vector p366 (ref. 24) and replaced with an 839-bp BglII-StuI TRP1 fragment. A BamHI-XhoI fragment containing sas2Δ::TRP1 was isolated for integrative disruption transformation [Rothstein, R. (1991), *Meth. Enzym.* 194:281–301]. The sas3Δ::URA3 construct (pLP264) and SAS3 in pGEM-7Z+ (pLP263) were both kindly provided by B. Scherens [Scherens, B. et al. (1993) *Yeast* 9:1355–1371]. The sas3Δ::HIS3 allele was constructed as follows: a 3.7-kb KpnI-EcoRI fragment of pLP263 was subcloned into pKS+ Bluescript (Stratagene) to create pLP266. pLP266 was digested with EcoRV to remove a 1.9-kb fragment and was then ligated to a 1.76-kb BamHI HIS3 fragment that had been blunted with Klenow. The resulting plasmid, pLP313, was digested with EcoRI and BsrGI to release a 3.57-kb sas3Δ::HIS3 fragment used for integrative disruption transformation. All disruptions were confirmed by genomic blotting analysis.

Example 5

Stationary Viability Assays

Strains were grown at 30° C. in rich liquid medium supplemented with adenine (20 mg/l). After 4 h, 1 d, 3 d, 5 d, 7 d, 10 d and 14 d, the expected CFU/ml of each strain was determined by haemocytometer counting, and appropriate dilutions were plated in triplicate. After 3 d at 30° C., the number of CFU/plate was counted, averaged, and compared to the expected CFU/plate. In our experiments, nat1 and ard1 phenotypes are indistinguishable, as previously reported [Mullen, J. R. et al. (1989) *EMBO J.* 8:2067–2075].

Example 6

Mutations in ESA1

A deletion of ESA1 was made in a diploid strain using PCR technology [Baudin, A. et al. (1993) *NAR* 14:3329–3330]. The heterozygous mutant diploid was transformed with a wild type copy of the gene, sporulated, and dissected. Haploid null mutants bearing the wild type gene on a plasmid were recovered. In separate experiments, a library of mutant ESA1 sequences was made using mutagenic PCR. These plasmids were then transferred into the ESA1 mutant strain and the wild type plasmid was evicted [Guthrie and Fink (eds.) *Methods in Enzymology*, 1994]. Transformants were tested for ability to grow at elevated temperatures. Those which were unable to grow were identified as temperature sensitive mutants. The yeast strains bearing the mutant plasmids are used in the assays above. A wild-type strain was able to survive and was viable at 360. Three mutant strains with decreased viability at 34° and total lack of viability at 36° were identified. LPY2879:Mata his3Δ200 leu2-3,112 trp1Δ1 ura3-52 ESA1 Δ: :HIS3 transformed with a plasmid bearing ESA1 [I368V][L394Q]; LPY2889:Mata his3Δ200 leu2-3,112 trp1Δ1 ura3-52 ESA1 Δ::HIS3 transformed with a plasmid bearing ESA1 [S375P][S378P]; LPY2877:Mata his3Δ200 leu2-3,112 trp1Δ1 ura3-52 ESA1 Δ::HIS3 transformed with a plasmid bearing ESA1 [S2P][L327P].

Example 7

ESA1 has acetyltransferase activity

ESA1 was tested for histone acetyltransferase activity using assays previously described [Brownell, J. and Allis, C., (1995) *PNAS* vol. 92, pp. 6364–6368; Brownell, J. E. et al. (1996) *Cell* 84:843–851]. Coding sequences of ESA1 were cloned into an E. coli expression vector (pRSET). Expression of the gene was induced and extracts were prepared. The extracts were incubated with calf thymus histones and [$^3$H]-acetyl-Coenzyme A. Radioactivity transferred to the histone substrate in an extract-dependent manner was quantified by liquid scintillation counting. Compared to positive (recombinant Gcn5p extracts) and negative (extract alone, histones without extract and comparable vector-only) controls, ESA1 has HAT activity.

TABLE 1

| | Sas2p | | Sas3p | | TIP60 | | Sp sas+ | | MOZ | |
|---|---|---|---|---|---|---|---|---|---|---|
| | P | % Identity (% Similarity) | P | % Identity (% Similarity) | P | % Identity (% Similarity) | P | % Identity (% Similarity) | P | % Identity (% Similarity) |
| Sas3p | $10^{-35}$ | 29% (54%) | | | | | | | | |
| TIP60 | $10^{-39}$ | 28% (50%) | $10^{-80}$ | 36% (57%) | | | | | | |
| Sp sas+ | $10^{-35}$ | 31% (53%) | $10^{-96}$ | 43% (62%) | $10^{-91}$ | 45% (60%) | | | | |
| MOZ | $10^{-31}$ | 31% (58%) | $10^{-80}$ | 30% (51%) | $10^{-94}$ | 39% (57%) | $10^{-86}$ | 42% (59%) | | |
| Esa1p | $10^{-33}$ | 30% (56%) | $10^{-77}$ | 35% (58%) | $10^{-114}$ | 62% (77%) | $10^{-82}$ | 49% (69%) | $10^{-116}$ | 64% (78%) |

TABLE 2

| | |
|---|---|
| SAS2 | LACILIFPPYQRRGLGLLLIEFSY |
| SAS3 | LSCILTLPIYQRKGYGQFLMEFSY |
| Esa1p | VACILTLPQYQRMGYGKLLIEFSY |
| TIP60 | VACILTLPPYQRRGYRKLLIEFSY |
| MOZ | VSCIMILPQYQRKGYGRFLIDFSY |
| Spsas+ | VSCILTLPIYQRRGYGVFLIDFSY |
| CegSAS | LSCIMTLPCYQEMGLGRFLIDISY |
| HAT1 | ISQFLIFPPYQNKGHGSCLYEAII |
| ErimI | LFNIAVDPDYQRQGLGRALLEHLI |
| HrimI | LFNIAILPTYQGCGFGKLLLGKLI |
| TtHATA1 | VAFLAVTANEQVRGYGTRLMNKFK |
| GCN5 | IVFCAISSTEQVRGYGAHLMNHLK |
| hGCN5 | IVFCAVTSNEQVKGYGTHLMNHLK |
| ARD1 | ITSLSVMRTYRRMGIAENLMRQAL |
| MAK3 | IGMLAVESTYRGHGIAKKLVEIAI |
| NAT2 | EEKIYLNRGKQLIGMGEPDESKVI |

The above partial amino acid sequences are given in SEQ ID NOS:7–22.

We claim:

1. A non-naturally occurring recombinant DNA molecule comprising a protein coding sequence, wherein the coding sequence hybridizes under conditions of medium stringency with an oligonucleotide comprising at least 25 continuous nucleotides of SEQ ID NO:5, from nucleotides 531–1865.

2. The non-naturally occurring recombinant DNA molecule of claim 1 wherein the silencing protein has the amino acid sequence as given in SEQ ID NO:6.

3. The non-naturally occurring recombinant DNA molecule of claim 1 wherein the coding sequence comprises nucleotides 531–1865 of SEQ ID NO:5.

4. The non-naturally occurring recombinant DNA molecule of claim 1 wherein the coding sequence is operably linked to control sequences capable of effecting expression of the coding sequence in a suitable expression host.

5. A strain of yeast containing a mutation in a gene encoding a silencing protein, said gene comprising a coding region that encodes a silencing protein wherein the coding region hybridizes under conditions of medium stringency with an oligonucleotide comprising at least 25 continuous nucleotides of nucleotide sequence SEQ ID NO: 1 and wherein said strain has a detectable phenotype resulting from the mutation in said gene encoding a silencing protein.

6. The strain of yeast of claim 5 wherein said yeast is *Saccharomyces cerevisiae*.

7. A strain of yeast containing a mutation in a gene encoding a silencing protein, said gene comprising a coding region that encodes a silencing protein, said coding region hybridizing under conditions of medium stringency with an oligonucleotide comprising at least 25 continuous nucleotides of nucleotide sequence SEQ ID NO:5 and wherein said strain has a detectable phenotype resulting from the mutation in said gene encoding a silencing protein.

8. The strain of yeast of claim 7, wherein said yeast is *Saccharomyces cerevisiae*.

* * * * *

```
                        SEQUENCE LISTING (1) GENERAL INFORMATION:

(iii) NUMBER OF SEQUENCES: 25

(2) INFORMATION FOR SEQ ID NO:1:

(i) SEQUENCE CHARACTERISTICS:
        (A) LENGTH: 4906 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (vi) ORIGINAL SOURCE:
        (A) ORGANISM: Saccharomyces cerevisiae (ix) FEATURE:
        (A) NAME/KEY: CDS
        (B) LOCATION: 1712..2728

(xi) SEQUENCE DESCRIPTION: SEQ ID NO:1:

CACCTTAAAA TACCTATAAG AATCATATCT TCTCTTCCAT ACCACCAAAG CTCACCCAAT     60

GAACCACCAA TACAATCGTA ACTAGCTAAC CTAACCTACC ACTAACCACT ACAACCACCA    120

TATAATTAAG CGATATAAAT ATCCATATTT CTATTACATC TAGTATAACA AGGAAATAAA    180

TATCCTCGAT CATACGAACC ACCACATTAG GCGATCGCTA TCTCGTCCTA TAATATATTG    240

GGGATGGTGA TGCTGTCCTT GACGTGCCCT TGTGACGGGG GGCGATTGTC GGTCATTAGG    300

ACTACGTGCT TCAGTGAGAG GTTCAAGAAT TTCCGCATTG GCATTTGGCT CCGTAGTAGA    360
```

```
ACTCTCAGCG GGAGCTGAAT CTGGGTTTTC TACTCTTTCA TCGTTTTCAT CCTGTCTAGT     420

GAACTGCTTA TTCCTAATTC TTTTCAGTTC TTTTAATTTG GCCATATGGC CGGATCTGGC     480

TTTTTCATTA AACCTTTTTC TGTAAGTACC CATACTTATA TTTCTTAAGA CACTCTATTA     540

TTAGTATTGG GTTGTAATTG CATTTTTATA GCATATAGCA CTTGCTATTA ACAATAATAT     600

ACTAATACTA TAATGAGCTT TCAATACTCA GCTCATCGCC AATGAAAATT TTCGGAACAC     660

CCAATCATCA TGATATGTTA GGCGCGTAAA TATGAAGAAT AACAGAATCG TTAATCAGAA     720

GAGATGATGA AATCATTAAG TCTTGTCCAT ATCGAACTGG ATAGAGTATG TAGCGCTCTA     780

AGAATCTGTT AAATTGAAGT TTGATTTTTT GATATTGGAG GCTCCTATTT TCTAGTTGCT     840

TTTTGTTTTC ACTCGCAAAA AAAATAAGAA TCATATCTTC TCTTCCATAC CACCAAAGCT     900

CACCCAATGA ACCACCAATA CAATCGTAAC TAGCTAACCT AACCTACCAC TAACCACTAC     960

AACCACCATA TAATTAAGCG ATATAAATAT CCATATTTCT ATTACATCTA GTATAACAAG    1020

GAAATAAATA TCCTCGATCA TACGAACCAC CACATTAGGC GATCGCTATC TCGTCCTATA    1080

ATATATTGGG GATGGTGATG CTGTCCTTGA CGTGCCCTTG TGACGGGGGG CGATTGTCGG    1140

TCATTAGGAC TACGTGCTTC AGTGAGAGGT TCAAGAATTT CCGCATTGGC ATTTGGCTCC    1200

GTAGTAGAAC TCTCAGCGGG AGCTGAATCT GGGTTTTCTA CTCTTTCATC GTTTTCATCC    1260

TGTCTAGTGA ACTGCTTATT CCTAATTCTT TTCAGTTCTT TTAATTTGGC CATATGGCCG    1320

GATCTGGCTT TTTCATTAAA CCTTTTTCTG TAAGTACCCA TACTTATATT TCTTAAGACA    1380

CTCTATTATT AGTATTGGGT TGTAATTGCA TTTTTATAGC ATATAGCACT TGCTATTAAC    1440

AATAATATAC TAATACTATA TGAGCTTTC AATACTCAGC TCATCGCCAA TGAAAATTTT    1500

CGGAACACCC AATCATCATG ATATGTTAGG CGCGTAAATA TGAAGAATAA CAGAATCGTT    1560

AATCAGAAGA GATGATGAAA TCATTAAGTC TTGTCCATAT CGAACTGGAT AGAGTATGTA    1620

GCGCTCTAAG AATCTGTTAA ATTGAAGTTT GATTTTTGA TATTGGAGGC TCCTATTTTC    1680

TAGTTGCTTT TTGTTTTCAC TCGCAAAAAA A ATG GCA AGA TCT TTA AGT CAA      1732
                                  Met Ala Arg Ser Leu Ser Gln
                                    1               5

TCA CTC ACA GCG ACT ACC CAG AAG CTA AAA GGA AAG AAG AAT GGT GGA      1780
Ser Leu Thr Ala Thr Thr Gln Lys Leu Lys Gly Lys Lys Asn Gly Gly
         10                  15                  20

AAA GGC AAG AAT AAG CCC TCA GCA AAA ATT AAA AAA ACT CAA AAA GAG      1828
Lys Gly Lys Asn Lys Pro Ser Ala Lys Ile Lys Lys Thr Gln Lys Glu
     25                  30                  35

ATG CTA TAT GGA ATA CTG AAC GAA AGG AAC ATA AGA CAG ATT CAG TTT      1876
Met Leu Tyr Gly Ile Leu Asn Glu Arg Asn Ile Arg Gln Ile Gln Phe
 40                  45                  50                  55

GGA CTG AAT AAA AAA TTC TCT ACT TGG TAT GGG AGC GCC GTT TAT TTC      1924
Gly Leu Asn Lys Lys Phe Ser Thr Trp Tyr Gly Ser Ala Val Tyr Phe
             60                  65                  70

GAT CCT GAA ACA AAA AGG CTA GGG TGC TCC GAG ACC AAG GGT CAG CTT      1972
Asp Pro Glu Thr Lys Arg Leu Gly Cys Ser Glu Thr Lys Gly Gln Leu
                 75                  80                  85

TCC TCT GTT TCT AAC AGC CAA TAC TGG CTA GAC ACT CTT TTC GTT TGT      2020
Ser Ser Val Ser Asn Ser Gln Tyr Trp Leu Asp Thr Leu Phe Val Cys
                     90                  95                 100

GAA TAC TGC TTC AAA TAC ACG GAT GAT CAG ACG CGG TTT GTA GGA CAT      2068
Glu Tyr Cys Phe Lys Tyr Thr Asp Asp Gln Thr Arg Phe Val Gly His
        105                 110                 115

GTT GCA AGT TGT CCA TTT CAA TAT CGT GTT CCA GGC AAA ATA AAA TAC      2116
Val Ala Ser Cys Pro Phe Gln Tyr Arg Val Pro Gly Lys Ile Lys Tyr
120                 125                 130                 135
```

| | | |
|---|---|---|
| AAG AGT CCT GAA TAT ACA ATA AGA AGA GTA AAA GGA TCC AAG TAT CAA<br>Lys Ser Pro Glu Tyr Thr Ile Arg Arg Val Lys Gly Ser Lys Tyr Gln<br>140 145 150 | | 2164 |
| CTC TTT TGC CAA TGT CTT TGT CTT TTC ACT AAG CTA TAT CTG GAC AAT<br>Leu Phe Cys Gln Cys Leu Cys Leu Phe Thr Lys Leu Tyr Leu Asp Asn<br>155 160 165 | | 2212 |
| AAA TCC ATG TAT TTC AAA GTA GAT CAT TAT GAA TTT TAC ATA GTT TAT<br>Lys Ser Met Tyr Phe Lys Val Asp His Tyr Glu Phe Tyr Ile Val Tyr<br>170 175 180 | | 2260 |
| GAA ACT GGA TCA ACA AAG CCG ATG GGA TTC TTT TCG AAA GAT TTA GTG<br>Glu Thr Gly Ser Thr Lys Pro Met Gly Phe Phe Ser Lys Asp Leu Val<br>185 190 195 | | 2308 |
| TCA TAT CAG CAA AAT AAT CTA GCG TGC ATC TTG ATA TTT CCC CCA TAT<br>Ser Tyr Gln Gln Asn Asn Leu Ala Cys Ile Leu Ile Phe Pro Pro Tyr<br>200 205 210 215 | | 2356 |
| CAA CGA CGT GGA TTA GGC CTT TTA CTT ATC GAG TTT TCA TAC AAA CTA<br>Gln Arg Arg Gly Leu Gly Leu Leu Leu Ile Glu Phe Ser Tyr Lys Leu<br>220 225 230 | | 2404 |
| TCC CAA TTA GAA GGT GTA ATA TCA GGG CCA GAA GTA CCG TTA TCA CCT<br>Ser Gln Leu Glu Gly Val Ile Ser Gly Pro Glu Val Pro Leu Ser Pro<br>235 240 245 | | 2452 |
| TTT GGA CTA ATC GGG TAC TTG AAA TAT TGG TCA CAG ATA CTC TGT TGG<br>Phe Gly Leu Ile Gly Tyr Leu Lys Tyr Trp Ser Gln Ile Leu Cys Trp<br>250 255 260 | | 2500 |
| CAC CTT ATT GAA GGT GAC CTC GCC CAT TAT GAT AAA GTG ACC CTG GAG<br>His Leu Ile Glu Gly Asp Leu Ala His Tyr Asp Lys Val Thr Leu Glu<br>265 270 275 | | 2548 |
| GAT CTT TCC ATC GTG ACT GGA ATG AGA GTC AAT GAT GTT ATT TTG ACC<br>Asp Leu Ser Ile Val Thr Gly Met Arg Val Asn Asp Val Ile Leu Thr<br>280 285 290 295 | | 2596 |
| TTG AAG CAC TTG AAC TGT ATT GGG GAG AAT AAC CAA ATT TAC TTG CAG<br>Leu Lys His Leu Asn Cys Ile Gly Glu Asn Asn Gln Ile Tyr Leu Gln<br>300 305 310 | | 2644 |
| TCA TTG AAT AGC TGG TTG AAA CTA CAT GGA ACA AAA CGG AAT TGG TTC<br>Ser Leu Asn Ser Trp Leu Lys Leu His Gly Thr Lys Arg Asn Trp Phe<br>315 320 325 | | 2692 |
| AAA TTA AAA GAT GAA TAT TTG CTG ATA GAT GAC TAG GAATCTATTC<br>Lys Leu Lys Asp Glu Tyr Leu Leu Ile Asp Asp *<br>330 335 | | 2738 |

AGGATGTAAC TTAATGGCAT ATGTATTTCA GGATAGAATA TCGCTCGATG AATTCCTGTA 2798

CAGACAACTA CAAACGGACG AATTTTGTCT GACCAAGTTA AGAACAGAGA ACTAATGCAT 2858

AAAATTTGTT TTGCTGCAAA AGTTTCCCTT TTTTTAGAGT ATAAATATCT TTTATAGCAA 2918

AAGACTTAAA ACAGGTTCAC GTTTTTATTA GCCGTTTTTG GGCCGGTTTT TCGATGACGA 2978

ACAAGGACCA AACAAATACA GCATCAAAAC AAATTCTAGA ATAAGAAGGC AGAAAGGGTA 3038

AGGGCATAAA GGAAACCTTC TTTTGTGGTG ATGTTGAACT GGGTTTAGCC AAAATTACAA 3098

CACATATTAA AGTTTTGTTA TTTTGCGATA AAGTTATTGC TCTTGAGCAT CAAAGAAAGT 3158

GGGAGGTTAA ACAGAGGAAA ACACATTGAA ATTTATTCAA AAAAAGATAC CGCTATACAA 3218

CTTTGGCCTG ATACTATCTA TAGACACGAG TGTCCATACT TAGCAGTAGA TGTCCGGATT 3278

CGCAAAACTC AAGTCGTGGT TATACAAAGC TTGCAAGATC TTTAAGTCAA TCACTCACAG 3338

CGACTACCCA GAAGCTAAAA GGAAAGAAGA ATGGTGGAAA AGGCAAGAAT AAGCCCTCAG 3398

CAAAAATTAA AAAAACTCAA AAAGAGATGC TATATGGAAT ACTGAACGAA AGGAACATAA 3458

GACAGATTCA GTTTGGACTG AATAAAAAAT TCTCTACTTG GTATGGGAGC GCCGTTTATT 3518

TCGATCCTGA AACAAAAAGG CTAGGGTGCT CCGAGACCAA GGGTCAGCTT TCCTCTGTTT 3578

```
CTAACAGCCA ATACTGGCTA GACACTCTTT TCGTTTGTGA ATACTGCTTC AAATACACGG      3638

ATGATCAGAC GCGGTTTGTA GGACATGTTG CAAGTTGTCC ATTTCAATAT CGTGTTCCAG      3698

GCAAAATAAA ATACAAGAGT CCTGAATATA CAATAAGAAG AGTAAAAGGA TCCAAGTATC      3758

AACTCTTTTG CCAATGTCTT TGTCTTTTCA CTAAGCTATA TCTGGACAAT AAATCCATGT      3818

ATTTCAAAGT AGATCATTAT GAATTTTACA TAGTTTATGA AACTGGATCA ACAAAGCCGA      3878

TGGGATTCTT TTCGAAAGAT TTAGTGTCAT ATCAGCAAAA TAATCTAGCG TGCATCTTGA      3938

TATTTCCCCC ATATCAACGA CGTGGATTAG GCCTTTTACT TATCGAGTTT TCATACAAAC      3998

TATCCCAATT AGAAGGTGTA ATATCAGGGC CAGAAGTACC GTTATCACCT TTTGGACTAA      4058

TCGGGTACTT GAAATATTGG TCACAGATAC TCTGTTGGCA CCTTATTGAA GGTGACCTCG      4118

CCCATTATGA TAAAGTGACC CTGGAGGATC TTTCCATCGT GACTGGAATG AGAGTCAATG      4178

ATGTTATTTT GACCTTGAAG CACTTGAACT GTATTGGGGA GAATAACCAA ATTTACTTGC      4238

AGTCATTGAA TAGCTGGTTG AAACTACATG GAACAAAACG GAATTGGTTC AAATTAAAAG      4298

ATGAATATTT GCTGATAGAT GACTAGGAAT CTATTCAGGA TGTAACTTAA TGGCATATGT      4358

ATTTCAGGAT AGAATATCGC TCGATGAATT CCTGTACAGA CAACTACAAA CGGACGAATT      4418

TTGTCTGACC AAGTTAAGAA CAGAGAACTA ATGCATAAAA TTTGTTTTGC TGCAAAAGTT      4478

TCCCTTTTTT TAGAGTATAA ATATCTTTTA TAGCAAAAGA CTTAAAACAG GTTCACGTTT      4538

TTATTAGCCG TTTTTGGGCC GGTTTTTCGA TGACGAACAA GGACCAAACA AATACAGCAT      4598

CAAAACAAAT TCTAGAATAA GAAGGCAGAA AGGGTAAGGG CATAAAGGAA ACCTTCTTTT      4658

GTGGTGATGT TGAACTGGGT TTAGCCAAAA TTACAACACA TATTAAAGTT TTGTTATTTT      4718

GCGATAAAGT TATTGCTCTT GAGCATCAAA GAAAGTGGGA GGTTAAACAG AGGAAAACAC      4778

ATTGAAATTT ATTCAAAAAA AGATACCGCT ATACAACTTT GGCCTGATAC TATCTATAGA      4838

CACGAGTGTC CATACTTAGC AGTAGATGTC CGGATTCGCA AAACTCAAGT CGTGGTTATA      4898

CAAAGCTT                                                              4906
```

(2) INFORMATION FOR SEQ ID NO:2:

(i) SEQUENCE CHARACTERISTICS:
        (A) LENGTH: 338 amino acids
        (B) TYPE: amino acid
        (D) TOPOLOGY: linear (ii) MOLECULE TYPE: protein (xi) SEQUENCE DESCRIPTION: SEQ ID NO:2:

```
Met Ala Arg Ser Leu Ser Gln Ser Leu Thr Ala Thr Thr Gln Lys Leu
  1               5                  10                  15

Lys Gly Lys Lys Asn Gly Gly Lys Gly Lys Asn Lys Pro Ser Ala Lys
                 20                  25                  30

Ile Lys Lys Thr Gln Lys Glu Met Leu Tyr Gly Ile Leu Asn Glu Arg
             35                  40                  45

Asn Ile Arg Gln Ile Gln Phe Gly Leu Asn Lys Phe Ser Thr Trp
         50                  55                  60

Tyr Gly Ser Ala Val Tyr Phe Asp Pro Glu Thr Lys Arg Leu Gly Cys
 65                  70                  75                  80

Ser Glu Thr Lys Gly Gln Leu Ser Ser Val Ser Asn Ser Gln Tyr Trp
                 85                  90                  95

Leu Asp Thr Leu Phe Val Cys Glu Tyr Cys Phe Lys Tyr Thr Asp Asp
                100                 105                 110

Gln Thr Arg Phe Val Gly His Val Ala Ser Cys Pro Phe Gln Tyr Arg
```

```
                115                 120                 125
Val Pro Gly Lys Ile Lys Tyr Lys Ser Pro Glu Tyr Thr Ile Arg Arg
    130                 135                 140

Val Lys Gly Ser Lys Tyr Gln Leu Phe Cys Gln Cys Leu Cys Leu Phe
145                 150                 155                 160

Thr Lys Leu Tyr Leu Asp Asn Lys Ser Met Tyr Phe Lys Val Asp His
                165                 170                 175

Tyr Glu Phe Tyr Ile Val Tyr Glu Thr Gly Ser Thr Lys Pro Met Gly
                180                 185                 190

Phe Phe Ser Lys Asp Leu Val Ser Tyr Gln Gln Asn Asn Leu Ala Cys
            195                 200                 205

Ile Leu Ile Phe Pro Pro Tyr Gln Arg Arg Gly Leu Gly Leu Leu Leu
        210                 215                 220

Ile Glu Phe Ser Tyr Lys Leu Ser Gln Leu Glu Gly Val Ile Ser Gly
225                 230                 235                 240

Pro Glu Val Pro Leu Ser Pro Phe Gly Leu Ile Gly Tyr Leu Lys Tyr
                245                 250                 255

Trp Ser Gln Ile Leu Cys Trp His Leu Ile Glu Gly Asp Leu Ala His
                260                 265                 270

Tyr Asp Lys Val Thr Leu Glu Asp Leu Ser Ile Val Thr Gly Met Arg
            275                 280                 285

Val Asn Asp Val Ile Leu Thr Leu Lys His Leu Asn Cys Ile Gly Glu
    290                 295                 300

Asn Asn Gln Ile Tyr Leu Gln Ser Leu Asn Ser Trp Leu Lys Leu His
305                 310                 315                 320

Gly Thr Lys Arg Asn Trp Phe Lys Leu Lys Asp Glu Tyr Leu Leu Ile
                325                 330                 335

Asp Asp (2) INFORMATION FOR SEQ ID NO:3:

(i) SEQUENCE CHARACTERISTICS:
        (A) LENGTH: 3925 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (vi) ORIGINAL SOURCE:
        (A) ORGANISM: Saccharomyces cerevisiae (ix) FEATURE:
        (A) NAME/KEY: CDS
        (B) LOCATION: 1340..3835

(xi) SEQUENCE DESCRIPTION: SEQ ID NO:3:

ACTCTCCATC CGGTTATTCT GCCAACCATT ATCAAATCAA TTCCGTTAAT CCCTTACTGA    60

GAAATTCTCA AATTTCACCT CCAAATTCAC AAATCCCAAT CAACAGCCAA ACCCTATCCC   120

AAGCGCAACC ACCAGCACAG TCCCAAACTC AACAACGGGT ACCAGTGGCA TACCAAAATG   180

CTTCATTGTC TTCCCAGCAG TTGTACAACC TTAACGGCCC ATCTTCAGCA AACTCACAGT   240

CCCAACTGCT TCCACAGCAC ACAAATGGCT CAGTACATTC TAATTTCTCA TATCAGTCTT   300

ATCACGATGA GTCCATGTTG TCCGCACACA ATTTGAATAG TGCCGACTTG ATCTATAAAT   360

CTTTGAGTCA CTCTGGACTA GATGATGGCT TGGAACAGGG CTTGAATCGT TCTTTAAGCG   420

GACTGGATTT ACAAAACCAA AACAAGAAGA ATCTATGGTA ATATATACTT CCATTATTCT   480
```

```
ATGATTATAG AGTTTGTTTG GTATTTGTAT ATCGCACGAT ACAAGTAATG AGGGGTGCTT      540

ACACAAGATA AAAGATAAAA AAATATATAT ATATAATAAA AACCATCAAA AACACCATTG      600

AAAAAAAATA TAAAAAAAAA AAAAAATAAC CGAATATGAA TATGAAATTA ATGATCATGA      660

TGAAGTTAAT TTTTACTGAG AAACGTCACC TAATGTCGAT GAAACGATGA TAATGAATGA      720

ATGATGAGGC TACTTTAAGT AACGCAATGT AATCAAGCCA AAATTATCCC TCTTTTTTTT      780

TTTTCCCTCT TTTGAGATTT TATTTTTAAC CTACTACTTA CTTTTTTTTT TTGAACGTTC      840

TTTTCCCACA TACTTTTATA TATGGTATTT ATATGTACGA TGTTTAATCA CAGAGATGTT      900

TCTACCTTAC TCGATATTGT TTTTGCATTA ATTGATATCT TGCTCACTGC ATCATTGGCG      960

GTATTTGTAG TATATAGAAA GTCGGGTAAC AATAATTTAT TGACATTTCT TTGTTTACAA     1020

TGATCAGAGA AGAGCAGAAA GTTTCATAGT CAAACGTTCA GGCCAATTGA ACAAGAAATT     1080

ATTCGTTTTT TTAGTCGTTG AGTGTTCAAC TGACATGCTA TTTTGGTGGT TCTTGATTAA     1140

TTGGGGGCTT CATTGTTTGA AATAAAGAGT CGGGAAAATA GCACAGAAAC AAAGCATATT     1200

AAAGAGGCA AAAGAAGAAA GAACGAATAT AAAAGGTAAA AAAGGAAAAG CATTGCTATT      1260

CTTTTCTCAT AGGTGTTATT CATACCGCCC TCTCTCTTCT TCCTTCTTCA TTAATTAGTC     1320

TCCGTATAAT TTGCAGATA ATG TCA TTA ACA GCA AAC GAC GAA TCG CCA AAA     1372
               Met Ser Leu Thr Ala Asn Asp Glu Ser Pro Lys
                 1               5                  10

CCC AAA AAA AAT GCA TTA TTG AAA AAC TTA GAG ATC GAT GAT CTG ATA       1420
Pro Lys Lys Asn Ala Leu Leu Lys Asn Leu Glu Ile Asp Asp Leu Ile
            15                  20                  25

CAT TCT CAA TTT GTC AGA AGC GAT ACA AAT GGA CAT AGA ACT ACA AGA       1468
His Ser Gln Phe Val Arg Ser Asp Thr Asn Gly His Arg Thr Thr Arg
        30                  35                  40

CGA CTA TTC AAC TCC GAT GCC AGT ATA TCA CAT CGA ATA AGA GGA AGT       1516
Arg Leu Phe Asn Ser Asp Ala Ser Ile Ser His Arg Ile Arg Gly Ser
    45                  50                  55

GTT CGG TCT GAT AAA GGC CTT AAT AAA ATA AAA AAA GGG TTG ATT TCC       1564
Val Arg Ser Asp Lys Gly Leu Asn Lys Ile Lys Lys Gly Leu Ile Ser
60                  65                  70                  75

CAG CAG TCC AAA CTT GCG TCA GAA AAT TCT TCT CAA AAT ATC GTT AAT       1612
Gln Gln Ser Lys Leu Ala Ser Glu Asn Ser Ser Gln Asn Ile Val Asn
            80                  85                  90

AGG GAC AAT AAG ATG GGA GCA GTA AGT TTC CCC ATT ATT GAA CCT AAT       1660
Arg Asp Asn Lys Met Gly Ala Val Ser Phe Pro Ile Ile Glu Pro Asn
        95                  100                 105

ATT GAA GTC AGC GAG GAG TTG AAG GTT AGA ATT AAG TAT GAT TCT ATC       1708
Ile Glu Val Ser Glu Glu Leu Lys Val Arg Ile Lys Tyr Asp Ser Ile
    110                 115                 120

AAA TTT TTC AAT TTT GAA AGA CTA ATA TCT AAA TCT TCA GTC ATA GCA       1756
Lys Phe Phe Asn Phe Glu Arg Leu Ile Ser Lys Ser Ser Val Ile Ala
125                 130                 135

CCT TTA GTT AAC AAA AAT ATA ACA TCA TCC GGT CCT CTA ATC GGG TTT       1804
Pro Leu Val Asn Lys Asn Ile Thr Ser Ser Gly Pro Leu Ile Gly Phe
140                 145                 150                 155

CAA AGA AGA GTT AAC AGG TTA AAG CAA ACA TGG GAT CTA GCA ACC GAA       1852
Gln Arg Arg Val Asn Arg Leu Lys Gln Thr Trp Asp Leu Ala Thr Glu
            160                 165                 170

AAC ATG GAG TAC CCA TAT TCT TCT GAT AAT ACG CCA TTC AGG GAT AAC       1900
Asn Met Glu Tyr Pro Tyr Ser Ser Asp Asn Thr Pro Phe Arg Asp Asn
        175                 180                 185

GAT TCT TGG CAA TGG TAC GTA CCA TAC GGC GGA ACA ATA AAA AAA ATG       1948
Asp Ser Trp Gln Trp Tyr Val Pro Tyr Gly Gly Thr Ile Lys Lys Met
    190                 195                 200
```

```
AAA GAT TTC AGT ACA AAA AGA ACT TTA CCC ACC TGG GAA GAT AAA ATA         1996
Lys Asp Phe Ser Thr Lys Arg Thr Leu Pro Thr Trp Glu Asp Lys Ile
    205                 210                 215

AAG TTT CTT ACA TTT TTA GAA AAC TCT AAG TCT GCA ACG TAC ATT AAT         2044
Lys Phe Leu Thr Phe Leu Glu Asn Ser Lys Ser Ala Thr Tyr Ile Asn
220                 225                 230                 235

GGT AAC GTA TCA CTT TGC AAT CAT AAT GAA ACC GAT CAA GAA AAC GAA         2092
Gly Asn Val Ser Leu Cys Asn His Asn Glu Thr Asp Gln Glu Asn Glu
                240                 245                 250

GAT AGG AAA AAA AGG AAA GGG AAA GTA CCA AGA ATC AAA AAT AAA GTG         2140
Asp Arg Lys Lys Arg Lys Gly Lys Val Pro Arg Ile Lys Asn Lys Val
            255                 260                 265

TGG TTT TCC CAG ATA GAA TAC ATT GTT CTT CGA AAT TAT GAA ATT AAA         2188
Trp Phe Ser Gln Ile Glu Tyr Ile Val Leu Arg Asn Tyr Glu Ile Lys
        270                 275                 280

CCT TGG TAT ACA TCT CCT TTT CCG GAA CAC ATC AAC CAA AAT AAA ATG         2236
Pro Trp Tyr Thr Ser Pro Phe Pro Glu His Ile Asn Gln Asn Lys Met
    285                 290                 295

GTT TTT ATA TGT GAG TTC TGC CTA AAA TAT ATG ACT TCT CGA TAT ACT         2284
Val Phe Ile Cys Glu Phe Cys Leu Lys Tyr Met Thr Ser Arg Tyr Thr
300                 305                 310                 315

TTT TAT AGA CAC CAA CTA AAG TGT CTA ACT TTT AAG CCC CCC GGA AAT         2332
Phe Tyr Arg His Gln Leu Lys Cys Leu Thr Phe Lys Pro Pro Gly Asn
                320                 325                 330

GAA ATT TAT CGC GAC GGT AAG CTG TCT GTT TGG GAA ATT GAT GGG CGG         2380
Glu Ile Tyr Arg Asp Gly Lys Leu Ser Val Trp Glu Ile Asp Gly Arg
            335                 340                 345

GAG AAT GTC TTG TAT TGT CAA AAT CTT TGC CTG TTG GCA AAA TGT TTT         2428
Glu Asn Val Leu Tyr Cys Gln Asn Leu Cys Leu Leu Ala Lys Cys Phe
        350                 355                 360

ATC AAT TCT AAG ACT TTG TAT TAC GAT GTT GAA CCG TTT ATA TTC TAT         2476
Ile Asn Ser Lys Thr Leu Tyr Tyr Asp Val Glu Pro Phe Ile Phe Tyr
    365                 370                 375

ATT CTA ACG GAG AGA GAG GAT ACA GAG AAC CAT CCC TAT CAA AAC GCA         2524
Ile Leu Thr Glu Arg Glu Asp Thr Glu Asn His Pro Tyr Gln Asn Ala
380                 385                 390                 395

GCC AAA TTC CAT TTC GTA GGC TAT TTC TCC AAG GAA AAA TTC AAC TCC         2572
Ala Lys Phe His Phe Val Gly Tyr Phe Ser Lys Glu Lys Phe Asn Ser
                400                 405                 410

AAT GAC TAT AAC CTA AGT TGT ATT TTA ACT CTA CCC ATA TAC CAG AGG         2620
Asn Asp Tyr Asn Leu Ser Cys Ile Leu Thr Leu Pro Ile Tyr Gln Arg
            415                 420                 425

AAA GGA TAT GGT CAG TTT TTG ATG GAA TTT TCA TAT TTA TTA TCC AGA         2668
Lys Gly Tyr Gly Gln Phe Leu Met Glu Phe Ser Tyr Leu Leu Ser Arg
        430                 435                 440

AAG GAG TCA AAA TTT GGA ACT CCT GAA AAA CCA TTG TCG GAT TTA GGA         2716
Lys Glu Ser Lys Phe Gly Thr Pro Glu Lys Pro Leu Ser Asp Leu Gly
    445                 450                 455

TTA TTG ACT TAC AGA ACG TTT TGG AAG ATA AAA TGT GCT GAA GTG CTA         2764
Leu Leu Thr Tyr Arg Thr Phe Trp Lys Ile Lys Cys Ala Glu Val Leu
460                 465                 470                 475

TTA AAA TTA AGA GAC AGT GCT AGA CGT CGA TCA AAT AAT AAA AAT GAA         2812
Leu Lys Leu Arg Asp Ser Ala Arg Arg Arg Ser Asn Asn Lys Asn Glu
                480                 485                 490

GAT ACT TTT CAG CAG GTT AGC CTA AAC GAT ATC GCT AAA CTA ACA GGA         2860
Asp Thr Phe Gln Gln Val Ser Leu Asn Asp Ile Ala Lys Leu Thr Gly
            495                 500                 505

ATG ATA CCA ACA GAC GTT GTG TTT GGA TTG GAA CAA CTT CAA GTT TTG         2908
Met Ile Pro Thr Asp Val Val Phe Gly Leu Glu Gln Leu Gln Val Leu
        510                 515                 520
```

```
TAT CGC CAT AAA ACA CGC TCA TTA TCC AGT TTG GAT GAT TTC AAC TAT       2956
Tyr Arg His Lys Thr Arg Ser Leu Ser Ser Leu Asp Asp Phe Asn Tyr
        525                 530                 535

ATT ATT AAA ATC GAT TCT TGG AAC AGG ATT GAA AAT ATT TAC AAA ACT       3004
Ile Ile Lys Ile Asp Ser Trp Asn Arg Ile Glu Asn Ile Tyr Lys Thr
540                 545                 550                 555

TGG AGC TCA AAA AAC TAT CCT CGC GTC AAA TAT GAC AAA CTA TTG TGG       3052
Trp Ser Ser Lys Asn Tyr Pro Arg Val Lys Tyr Asp Lys Leu Leu Trp
                560                 565                 570

GAA CCT ATT ATA TTA GGG CCG TCA TTT GGT ATA AAT GGG ATG ATG AAC       3100
Glu Pro Ile Ile Leu Gly Pro Ser Phe Gly Ile Asn Gly Met Met Asn
        575                 580                 585

TTA GAA CCC ACC GCA TTA GCG GAC GAA GCT CTT ACA AAT GAA ACT ATG       3148
Leu Glu Pro Thr Ala Leu Ala Asp Glu Ala Leu Thr Asn Glu Thr Met
590                 595                 600

GCT CCG GTA ATT TCG AAT AAC ACA CAT ATA GAA AAC TAT AAC AAC AGT       3196
Ala Pro Val Ile Ser Asn Asn Thr His Ile Glu Asn Tyr Asn Asn Ser
                605                 610                 615

AGA GCA CAT AAT AAA CGC AGA AGA AGA AGA AGA AGT AGT GAG CAC           3244
Arg Ala His Asn Lys Arg Arg Arg Arg Arg Arg Ser Ser Glu His
620                 625                 630                 635

AAA ACA TCC AAG CTT CAT GTA AAC AAT ATC ATA GAA CCG GAA GTA CCT       3292
Lys Thr Ser Lys Leu His Val Asn Asn Ile Ile Glu Pro Glu Val Pro
                640                 645                 650

GCT ACT GAT TTT TTT GAA GAC ACT GTT TCC TCC TTA ACA GAG TAT ATG       3340
Ala Thr Asp Phe Phe Glu Asp Thr Val Ser Ser Leu Thr Glu Tyr Met
        655                 660                 665

TGT GAT TAT AAG AAC ACA AAT AAT GAT AGA TTA ATC TAT CAA GCG GAA       3388
Cys Asp Tyr Lys Asn Thr Asn Asn Asp Arg Leu Ile Tyr Gln Ala Glu
670                 675                 680

AAA AGA GTG CTG GAA AGC ATC CAT GAT CGC AAA GGG ATA CCA AGA TCA       3436
Lys Arg Val Leu Glu Ser Ile His Asp Arg Lys Gly Ile Pro Arg Ser
        685                 690                 695

AAA TTT AGT ACA GAA ACT CAT TGG GAG CTC TGC TTC ACT ATT AAA AAC       3484
Lys Phe Ser Thr Glu Thr His Trp Glu Leu Cys Phe Thr Ile Lys Asn
700                 705                 710                 715

TCC GAA ACA CCA CTT GGA AAT CAT GCA GCT AGG AGA AAC GAT ACT GGA       3532
Ser Glu Thr Pro Leu Gly Asn His Ala Ala Arg Arg Asn Asp Thr Gly
                720                 725                 730

ATA TCA AGT TTA GAG CAG GAT GAA GTA GAA AAC GAT GTA GAT ACT GAA       3580
Ile Ser Ser Leu Glu Gln Asp Glu Val Glu Asn Asp Val Asp Thr Glu
        735                 740                 745

TTA TAT GTA GGT GAA AAC GCC AAA GAA GAT GAA GAC GAA GAC GAA GAC       3628
Leu Tyr Val Gly Glu Asn Ala Lys Glu Asp Glu Asp Glu Asp Glu Asp
                750                 755                 760

TTT ACC CTT GAT GAT GAC ATT GAG GAT GAG CAA ATA TCA GAA GAA AAT       3676
Phe Thr Leu Asp Asp Asp Ile Glu Asp Glu Gln Ile Ser Glu Glu Asn
765                 770                 775

GAT GAG GAG GAA GAC ACA TAT GAA GAA GAC AGT GAT GAT GAT GAG GAT       3724
Asp Glu Glu Glu Asp Thr Tyr Glu Glu Asp Ser Asp Asp Asp Glu Asp
780                 785                 790                 795

GGG AAG AGA AAA GGA CAA GAG CAG GAT GAA AAC GAT ATA GAA AGC CAC       3772
Gly Lys Arg Lys Gly Gln Glu Gln Asp Glu Asn Asp Ile Glu Ser His
                800                 805                 810

ATA AGG AAG GAG AGA GTC AGA AAA AGA AGA AAA ATA ACT CTA ATA GAG       3820
Ile Arg Lys Glu Arg Val Arg Lys Arg Arg Lys Ile Thr Leu Ile Glu
        815                 820                 825

GAT GAC GAA GAA TAA GCGGCGATGG GTATATATTG GATATAAGCA TATACATGTA       3875
Asp Asp Glu Glu  *
        830
```

ACATTATTAA TAGCAATAAG AACCCTTGTA GTCAATAGTA TTACAGAATT         3925

(2) INFORMATION FOR SEQ ID NO:4:

(i) SEQUENCE CHARACTERISTICS:
        (A) LENGTH: 831 amino acids
        (B) TYPE: amino acid
        (D) TOPOLOGY: linear (ii) MOLECULE TYPE: protein (xi) SEQUENCE DESCRIPTION: SEQ ID NO:4:

```
Met Ser Leu Thr Ala Asn Asp Glu Ser Pro Lys Pro Lys Asn Ala
 1               5                  10                  15

Leu Leu Lys Asn Leu Glu Ile Asp Asp Leu Ile His Ser Gln Phe Val
            20                  25                  30

Arg Ser Asp Thr Asn Gly His Arg Thr Thr Arg Arg Leu Phe Asn Ser
        35                  40                  45

Asp Ala Ser Ile Ser His Arg Ile Arg Gly Ser Val Arg Ser Asp Lys
 50                  55                  60

Gly Leu Asn Lys Ile Lys Lys Gly Leu Ile Ser Gln Gln Ser Lys Leu
 65                  70                  75                  80

Ala Ser Glu Asn Ser Ser Gln Asn Ile Val Asn Arg Asp Asn Lys Met
            85                  90                  95

Gly Ala Val Ser Phe Pro Ile Ile Glu Pro Asn Ile Glu Val Ser Glu
        100                 105                 110

Glu Leu Lys Val Arg Ile Lys Tyr Asp Ser Ile Lys Phe Phe Asn Phe
        115                 120                 125

Glu Arg Leu Ile Ser Lys Ser Val Ile Ala Pro Leu Val Asn Lys
        130                 135                 140

Asn Ile Thr Ser Ser Gly Pro Leu Ile Gly Phe Gln Arg Arg Val Asn
145                 150                 155                 160

Arg Leu Lys Gln Thr Trp Asp Leu Ala Thr Glu Asn Met Glu Tyr Pro
                165                 170                 175

Tyr Ser Ser Asp Asn Thr Pro Phe Arg Asp Asn Asp Ser Trp Gln Trp
                180                 185                 190

Tyr Val Pro Tyr Gly Gly Thr Ile Lys Lys Met Lys Asp Phe Ser Thr
            195                 200                 205

Lys Arg Thr Leu Pro Thr Trp Glu Asp Lys Ile Lys Phe Leu Thr Phe
210                 215                 220

Leu Glu Asn Ser Lys Ser Ala Thr Tyr Ile Asn Gly Asn Val Ser Leu
225                 230                 235                 240

Cys Asn His Asn Glu Thr Asp Gln Glu Asn Asp Arg Lys Lys Arg
                245                 250                 255

Lys Gly Lys Val Pro Arg Ile Lys Asn Lys Val Trp Phe Ser Gln Ile
            260                 265                 270

Glu Tyr Ile Val Leu Arg Asn Tyr Glu Ile Lys Pro Trp Tyr Thr Ser
        275                 280                 285

Pro Phe Pro Glu His Ile Asn Gln Asn Lys Met Val Phe Ile Cys Glu
        290                 295                 300

Phe Cys Leu Lys Tyr Met Thr Ser Arg Tyr Thr Phe Tyr Arg His Gln
305                 310                 315                 320

Leu Lys Cys Leu Thr Phe Lys Pro Pro Gly Asn Glu Ile Tyr Arg Asp
                325                 330                 335

Gly Lys Leu Ser Val Trp Glu Ile Asp Gly Arg Glu Asn Val Leu Tyr
                340                 345                 350
```

-continued

```
Cys Gln Asn Leu Cys Leu Leu Ala Lys Cys Phe Ile Asn Ser Lys Thr
        355                 360                 365
Leu Tyr Tyr Asp Val Glu Pro Phe Ile Phe Tyr Ile Leu Thr Glu Arg
        370                 375                 380
Glu Asp Thr Glu Asn His Pro Tyr Gln Asn Ala Ala Lys Phe His Phe
385                 390                 395                 400
Val Gly Tyr Phe Ser Lys Glu Lys Phe Asn Ser Asn Asp Tyr Asn Leu
                405                 410                 415
Ser Cys Ile Leu Thr Leu Pro Ile Tyr Gln Arg Lys Gly Tyr Gly Gln
                420                 425                 430
Phe Leu Met Glu Phe Ser Tyr Leu Leu Ser Arg Lys Glu Ser Lys Phe
            435                 440                 445
Gly Thr Pro Glu Lys Pro Leu Ser Asp Leu Gly Leu Leu Thr Tyr Arg
        450                 455                 460
Thr Phe Trp Lys Ile Lys Cys Ala Glu Val Leu Leu Lys Leu Arg Asp
465                 470                 475                 480
Ser Ala Arg Arg Arg Ser Asn Asn Lys Asn Glu Asp Thr Phe Gln Gln
                485                 490                 495
Val Ser Leu Asn Asp Ile Ala Lys Leu Thr Gly Met Ile Pro Thr Asp
                500                 505                 510
Val Val Phe Gly Leu Glu Gln Leu Gln Val Leu Tyr Arg His Lys Thr
            515                 520                 525
Arg Ser Leu Ser Ser Leu Asp Asp Phe Asn Tyr Ile Ile Lys Ile Asp
        530                 535                 540
Ser Trp Asn Arg Ile Glu Asn Ile Tyr Lys Thr Trp Ser Ser Lys Asn
545                 550                 555                 560
Tyr Pro Arg Val Lys Tyr Asp Lys Leu Leu Trp Glu Pro Ile Ile Leu
                565                 570                 575
Gly Pro Ser Phe Gly Ile Asn Gly Met Met Asn Leu Glu Pro Thr Ala
                580                 585                 590
Leu Ala Asp Glu Ala Leu Thr Asn Glu Thr Met Ala Pro Val Ile Ser
            595                 600                 605
Asn Asn Thr His Ile Glu Asn Tyr Asn Asn Ser Arg Ala His Asn Lys
        610                 615                 620
Arg Arg Arg Arg Arg Arg Ser Ser Glu His Lys Thr Ser Lys Leu
625                 630                 635                 640
His Val Asn Asn Ile Ile Glu Pro Glu Val Pro Ala Thr Asp Phe Phe
                645                 650                 655
Glu Asp Thr Val Ser Ser Leu Thr Glu Tyr Met Cys Asp Tyr Lys Asn
                660                 665                 670
Thr Asn Asn Asp Arg Leu Ile Tyr Gln Ala Glu Lys Arg Val Leu Glu
            675                 680                 685
Ser Ile His Asp Arg Lys Gly Ile Pro Arg Ser Lys Phe Ser Thr Glu
        690                 695                 700
Thr His Trp Glu Leu Cys Phe Thr Ile Lys Asn Ser Glu Thr Pro Leu
705                 710                 715                 720
Gly Asn His Ala Ala Arg Arg Asn Asp Thr Gly Ile Ser Ser Leu Glu
                725                 730                 735
Gln Asp Glu Val Glu Asn Asp Val Asp Thr Glu Leu Tyr Val Gly Glu
                740                 745                 750
Asn Ala Lys Glu Asp Glu Asp Glu Asp Phe Thr Leu Asp Asp
            755                 760                 765
Asp Ile Glu Asp Glu Gln Ile Ser Glu Glu Asn Asp Glu Glu Glu Asp
```

```
                      770              775             780
Thr Tyr Glu Glu Asp Ser Asp Asp Glu Asp Gly Lys Arg Lys Gly
785                 790                 795                 800

Gln Glu Gln Asp Glu Asn Asp Ile Glu Ser His Ile Arg Lys Glu Arg
                805                 810                 815

Val Arg Lys Arg Arg Lys Ile Thr Leu Ile Glu Asp Asp Glu Glu
                820                 825                 830

(2) INFORMATION FOR SEQ ID NO:5:

(i) SEQUENCE CHARACTERISTICS:
        (A) LENGTH: 2003 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (vi) ORIGINAL SOURCE:
        (A) ORGANISM: Saccharomyces cerevisiae (ix) FEATURE:
        (A) NAME/KEY: CDS
        (B) LOCATION: 531..1868

(xi) SEQUENCE DESCRIPTION: SEQ ID NO:5:

TACTCATGAC CTTACCTTCT TGATCTATTT CGTTGACCAA AAAGTCAGTA TAACGCTGCT     60

TAATTTGGCC TCTAAATCCT GGCAATTCTG GAGATAAGAA CAAAGTAATA CCGACATCTG    120

CTTCGTGAAT ACCATCTGCC TGAGTACGTT GCTCAATTTT CAACTTCTTT GCAGCATTTT    180

CGGAAGGTCC TACGTGAGCA TCAAGGGGTC TCTTTACAGT GGCTTCTGAG GAGTCAGACA    240

TGGCATGCAA CAGATATTGC TTTTTTCCTT GGGAAGGAAC AACGTGATTA TAATTAATCG    300

ATGAGCTGTA CCTATTGACT ATTTCATCAT TATTATAATG ATGGAAAATT TTCCAAATTA    360

CTACCCGCCC GTTGAAAAGA TGAAAACGGC TTCCGGCGGA GCAAATGCAA AACGAATATT    420

GCTAAAAGGT GTATATTATT ATAGTAATCA AGGAGAATA GAAAAGAGCT TTACCATTCT     480

TTAGACGCTT CCTGTGCTAC CATTCTCGGA ATACTGCAA GAAATCATCG ATG TCC        536
                                                      Met Ser
                                                        1

CAT GAC GGA AAA GAA GAA CCT GGT ATT GCC AAA AAG ATA AAC TCA GTA      584
His Asp Gly Lys Glu Glu Pro Gly Ile Ala Lys Lys Ile Asn Ser Val
        5                  10                  15

GAT GAT ATT ATT ATC AAA TGT CAA TGC TGG GTC CAA AAA AAT GAT GAA      632
Asp Asp Ile Ile Ile Lys Cys Gln Cys Trp Val Gln Lys Asn Asp Glu
         20                  25                  30

GAA CGA TTA GCT GAA ATT TTA TCC ATA AAC ACA AGA AAA GCA CCA CCA      680
Glu Arg Leu Ala Glu Ile Leu Ser Ile Asn Thr Arg Lys Ala Pro Pro
 35                  40                  45                  50

AAA TTC TAT GTT CAC TAT GTT AAT TAC AAC AAG CGT TTA GAT GAG TGG      728
Lys Phe Tyr Val His Tyr Val Asn Tyr Asn Lys Arg Leu Asp Glu Trp
                 55                  60                  65

ATT ACC ACT GAC AGA ATA AAC CTG GAT AAA GAA GTA CTA TAT CCG AAA      776
Ile Thr Thr Asp Arg Ile Asn Leu Asp Lys Glu Val Leu Tyr Pro Lys
             70                  75                  80

CTA AAG GCT ACT GAT GAA GAT AAT AAG AAA CAA AAA AAG AAG AAG GCA      824
Leu Lys Ala Thr Asp Glu Asp Asn Lys Lys Gln Lys Lys Lys Lys Ala
         85                  90                  95

ACA AAT ACT AGT GAA ACG CCA CAA GAC TCT CTG CAA GAT GGT GTA GAT      872
Thr Asn Thr Ser Glu Thr Pro Gln Asp Ser Leu Gln Asp Gly Val Asp
    100                 105                 110
```

-continued

```
GGT TTC TCA AGA GAA AAT ACG GAT GTT ATG GAC TTA GAT AAT CTA AAT      920
Gly Phe Ser Arg Glu Asn Thr Asp Val Met Asp Leu Asp Asn Leu Asn
115                 120                 125                 130

GTA CAG GGA ATA AAA GAT GAG AAC ATA TCA CAC GAG GAT GAG ATA AAA      968
Val Gln Gly Ile Lys Asp Glu Asn Ile Ser His Glu Asp Glu Ile Lys
                135                 140                 145

AAG CTT AGA ACC TCC GGC TCT ATG ACA CAA AAT CCA CAT GAG GTG GCT     1016
Lys Leu Arg Thr Ser Gly Ser Met Thr Gln Asn Pro His Glu Val Ala
            150                 155                 160

CGA GTT AGA AAT CTC AAT CGA ATC ATT ATG GGG AAA TAT GAA ATA GAA     1064
Arg Val Arg Asn Leu Asn Arg Ile Ile Met Gly Lys Tyr Glu Ile Glu
        165                 170                 175

CCA TGG TAC TTT TCT CCA TAT CCT ATT GAA TTA ACT GAT GAA GAT TTT     1112
Pro Trp Tyr Phe Ser Pro Tyr Pro Ile Glu Leu Thr Asp Glu Asp Phe
    180                 185                 190

ATA TAT ATC GAC GAT TTC ACG TTG CAG TAT TTT GGA TCT AAG AAA CAA     1160
Ile Tyr Ile Asp Asp Phe Thr Leu Gln Tyr Phe Gly Ser Lys Lys Gln
195                 200                 205                 210

TAC GAA CGC TAC AGG AAG AAA TGT ACA TTA AGA CAT CCG CCA GGA AAT     1208
Tyr Glu Arg Tyr Arg Lys Lys Cys Thr Leu Arg His Pro Pro Gly Asn
                215                 220                 225

GAA ATC TAC AGA GAC GAT TAT GTT TCA TTC TTT GAA ATC GAT GGT AGA     1256
Glu Ile Tyr Arg Asp Asp Tyr Val Ser Phe Phe Glu Ile Asp Gly Arg
            230                 235                 240

AAG CAA AGG ACT TGG TGT CGA AAC TTG TGT TTA CTT TCC AAA CTT TTC     1304
Lys Gln Arg Thr Trp Cys Arg Asn Leu Cys Leu Leu Ser Lys Leu Phe
        245                 250                 255

CTA GAT CAC AAA ACA TTA TAC TAT GAC GTT GAT CCG TTT TTG TTT TAT     1352
Leu Asp His Lys Thr Leu Tyr Tyr Asp Val Asp Pro Phe Leu Phe Tyr
    260                 265                 270

TGC ATG ACG AGA CGA GAT GAG TTG GGT CAC CAT CTG GTG GGA TAT TTT     1400
Cys Met Thr Arg Arg Asp Glu Leu Gly His His Leu Val Gly Tyr Phe
275                 280                 285                 290

TCC AAG GAA AAA GAA TCC GCG GAT GGT TAC AAT GTT GCA TGT ATC TTA     1448
Ser Lys Glu Lys Glu Ser Ala Asp Gly Tyr Asn Val Ala Cys Ile Leu
                295                 300                 305

ACA CTA CCA CAA TAC CAA AGG ATG GGA TAT GGT AAG TTA TTG ATT GAA     1496
Thr Leu Pro Gln Tyr Gln Arg Met Gly Tyr Gly Lys Leu Leu Ile Glu
            310                 315                 320

TTT TCG TAT GAA TTG TCG AAA AAG GAA AAC AAA GTT GGT TCT CCC GAG     1544
Phe Ser Tyr Glu Leu Ser Lys Lys Glu Asn Lys Val Gly Ser Pro Glu
        325                 330                 335

AAA CCT TTG TCT GAT TTG GGT CTC TTA TCC TAT AGA GCC TAT TGG TCG     1592
Lys Pro Leu Ser Asp Leu Gly Leu Leu Ser Tyr Arg Ala Tyr Trp Ser
    340                 345                 350

GAC ACT CTC ATA ACG CTA TTA GTG GAA CAC CAG AAG GAA ATT ACT ATA     1640
Asp Thr Leu Ile Thr Leu Leu Val Glu His Gln Lys Glu Ile Thr Ile
355                 360                 365                 370

GAC GAA ATA AGC TCC ATG ACT TCG ATG ACC ACT ACA GAT ATA TTA CAC     1688
Asp Glu Ile Ser Ser Met Thr Ser Met Thr Thr Thr Asp Ile Leu His
                375                 380                 385

ACA GCA AAG ACA CTG AAT ATC CTG CGA TAT TAC AAG GGT CAG CAT ATT     1736
Thr Ala Lys Thr Leu Asn Ile Leu Arg Tyr Tyr Lys Gly Gln His Ile
            390                 395                 400

ATT TTC CTG AAT GAA GAT ATT TTA GAT AGG TAC AAT CGA CTT AAA GCC     1784
Ile Phe Leu Asn Glu Asp Ile Leu Asp Arg Tyr Asn Arg Leu Lys Ala
        405                 410                 415

AAA AAG AGA AGG ACA ATA GAC CCT AAT AGA CTC ATA TGG AAA CCA CCG     1832
Lys Lys Arg Arg Thr Ile Asp Pro Asn Arg Leu Ile Trp Lys Pro Pro
    420                 425                 430
```

```
GTA TTT ACT GCC TCT CAG TTA CGC TTT GCC TGG TAA GCTATGTAGT              1878
Val Phe Thr Ala Ser Gln Leu Arg Phe Ala Trp  *
435                 440                 445

GCTTTCCTAA ACTTACATTC AAACAACTTC TAATGTAAAA GCTTTAAATA AATGAAATTT       1938

ACGTAAAACA ATCACTAATA TTCAACGAGA ACTCCAGTAT TCCTGTAAGT TAATACTCTT       1998

ACTTA                                                                  2003
```

(2) INFORMATION FOR SEQ ID NO:6:

(i) SEQUENCE CHARACTERISTICS:
        (A) LENGTH: 445 amino acids
        (B) TYPE: amino acid
        (D) TOPOLOGY: linear (ii) MOLECULE TYPE: protein (xi) SEQUENCE DESCRIPTION: SEQ ID NO:6:

```
Met Ser His Asp Gly Lys Glu Glu Pro Gly Ile Ala Lys Lys Ile Asn
 1               5                  10                  15

Ser Val Asp Asp Ile Ile Ile Lys Cys Gln Cys Trp Val Gln Lys Asn
                20                  25                  30

Asp Glu Glu Arg Leu Ala Glu Ile Leu Ser Ile Asn Thr Arg Lys Ala
            35                  40                  45

Pro Pro Lys Phe Tyr Val His Tyr Val Asn Tyr Asn Lys Arg Leu Asp
        50                  55                  60

Glu Trp Ile Thr Thr Asp Arg Ile Asn Leu Asp Lys Glu Val Leu Tyr
 65                  70                  75                  80

Pro Lys Leu Lys Ala Thr Asp Glu Asp Asn Lys Gln Lys Lys Lys
                85                  90                  95

Lys Ala Thr Asn Thr Ser Glu Thr Pro Gln Asp Ser Leu Gln Asp Gly
                100                 105                 110

Val Asp Gly Phe Ser Arg Glu Asn Thr Asp Val Met Asp Leu Asp Asn
            115                 120                 125

Leu Asn Val Gln Gly Ile Lys Asp Glu Asn Ile Ser His Glu Asp Glu
        130                 135                 140

Ile Lys Lys Leu Arg Thr Ser Gly Ser Met Thr Gln Asn Pro His Glu
145                 150                 155                 160

Val Ala Arg Val Arg Asn Leu Asn Arg Ile Ile Met Gly Lys Tyr Glu
                165                 170                 175

Ile Glu Pro Trp Tyr Phe Ser Pro Tyr Pro Ile Glu Leu Thr Asp Glu
                180                 185                 190

Asp Phe Ile Tyr Ile Asp Asp Phe Thr Leu Gln Tyr Phe Gly Ser Lys
            195                 200                 205

Lys Gln Tyr Glu Arg Tyr Arg Lys Lys Cys Thr Leu Arg His Pro Pro
        210                 215                 220

Gly Asn Glu Ile Tyr Arg Asp Asp Tyr Val Ser Phe Phe Glu Ile Asp
225                 230                 235                 240

Gly Arg Lys Gln Arg Thr Trp Cys Arg Asn Leu Cys Leu Leu Ser Lys
                245                 250                 255

Leu Phe Leu Asp His Lys Thr Leu Tyr Tyr Asp Val Asp Pro Phe Leu
            260                 265                 270

Phe Tyr Cys Met Thr Arg Arg Asp Glu Leu Gly His His Leu Val Gly
        275                 280                 285

Tyr Phe Ser Lys Glu Lys Glu Ser Ala Asp Gly Tyr Asn Val Ala Cys
        290                 295                 300
```

```
Ile Leu Thr Leu Pro Gln Tyr Gln Arg Met Gly Tyr Gly Lys Leu Leu
305                 310                 315                 320

Ile Glu Phe Ser Tyr Glu Leu Ser Lys Lys Glu Asn Lys Val Gly Ser
                325                 330                 335

Pro Glu Lys Pro Leu Ser Asp Leu Gly Leu Leu Ser Tyr Arg Ala Tyr
                340                 345                 350

Trp Ser Asp Thr Leu Ile Thr Leu Leu Val Glu His Gln Lys Glu Ile
                355                 360                 365

Thr Ile Asp Glu Ile Ser Ser Met Thr Ser Met Thr Thr Thr Asp Ile
            370                 375                 380

Leu His Thr Ala Lys Thr Leu Asn Ile Leu Arg Tyr Tyr Lys Gly Gln
385                 390                 395                 400

His Ile Ile Phe Leu Asn Glu Asp Ile Leu Asp Arg Tyr Asn Arg Leu
                405                 410                 415

Lys Ala Lys Lys Arg Arg Thr Ile Asp Pro Asn Arg Leu Ile Trp Lys
                420                 425                 430

Pro Pro Val Phe Thr Ala Ser Gln Leu Arg Phe Ala Trp
                435                 440                 445
```

(2) INFORMATION FOR SEQ ID NO:7:

(i) SEQUENCE CHARACTERISTICS:
        (A) LENGTH: 24 amino acids
        (B) TYPE: amino acid
        (C) STRANDEDNESS: single
        (D) TOPOLOGY: unknown (ii) MOLECULE TYPE: peptide (iii) HYPOTHETICAL: NO (xi) SEQUENCE DESCRIPTION: SEQ ID NO:7:

```
Leu Ala Cys Ile Leu Ile Phe Pro Pro Tyr Gln Arg Arg Gly Leu Gly
1               5                   10                  15

Leu Leu Leu Ile Glu Phe Ser Tyr
                20
```

(2) INFORMATION FOR SEQ ID NO:8:

(i) SEQUENCE CHARACTERISTICS:
        (A) LENGTH: 24 amino acids
        (B) TYPE: amino acid
        (C) STRANDEDNESS: single
        (D) TOPOLOGY: unknown (ii) MOLECULE TYPE: peptide (iii) HYPOTHETICAL: YES (xi) SEQUENCE DESCRIPTION: SEQ ID NO:8:

```
Leu Ser Cys Ile Leu Thr Leu Pro Ile Tyr Gln Arg Lys Gly Tyr Gly
1               5                   10                  15

Gln Phe Leu Met Glu Phe Ser Tyr
                20
```

(2) INFORMATION FOR SEQ ID NO:9:

(i) SEQUENCE CHARACTERISTICS:
        (A) LENGTH: 24 amino acids
        (B) TYPE: amino acid
        (C) STRANDEDNESS: single
        (D) TOPOLOGY: unknown (ii) MOLECULE TYPE: peptide (iii) HYPOTHETICAL: YES (xi) SEQUENCE DESCRIPTION: SEQ ID NO:9:

Val Ala Cys Ile Leu Thr Leu Pro Gln Tyr Gln Arg Met Gly Tyr Gly
1               5                   10                  15

Lys Leu Leu Ile Glu Phe Ser Tyr
            20

(2) INFORMATION FOR SEQ ID NO:10:

(i) SEQUENCE CHARACTERISTICS:
        (A) LENGTH: 24 amino acids
        (B) TYPE: amino acid
        (C) STRANDEDNESS: single
        (D) TOPOLOGY: unknown (ii) MOLECULE TYPE: peptide (iii) HYPOTHETICAL: YES (xi) SEQUENCE DESCRIPTION: SEQ ID NO:10:

Val Ala Cys Ile Leu Thr Leu Pro Pro Tyr Gln Arg Arg Gly Tyr Arg
1               5                   10                  15

Lys Leu Leu Ile Glu Phe Ser Tyr
            20

(2) INFORMATION FOR SEQ ID NO:11:

(i) SEQUENCE CHARACTERISTICS:
        (A) LENGTH: 24 amino acids
        (B) TYPE: amino acid
        (C) STRANDEDNESS: single
        (D) TOPOLOGY: unknown (ii) MOLECULE TYPE: peptide (iii) HYPOTHETICAL: YES (xi) SEQUENCE DESCRIPTION: SEQ ID NO:11:

Val Ser Cys Ile Met Ile Leu Pro Gln Tyr Gln Arg Lys Gly Tyr Gly
1               5                   10                  15

Arg Phe Leu Ile Asp Phe Ser Tyr
            20

(2) INFORMATION FOR SEQ ID NO:12:

(i) SEQUENCE CHARACTERISTICS:
        (A) LENGTH: 24 amino acids
        (B) TYPE: amino acid
        (C) STRANDEDNESS: single
        (D) TOPOLOGY: unknown (ii) MOLECULE TYPE: peptide (iii) HYPOTHETICAL: YES (xi) SEQUENCE DESCRIPTION: SEQ ID NO:12:

Val Ser Cys Ile Leu Thr Leu Pro Ile Tyr Gln Arg Arg Gly Tyr Gly
1               5                   10                  15

Val Phe Leu Ile Asp Phe Ser Tyr
            20

(2) INFORMATION FOR SEQ ID NO:13:

(i) SEQUENCE CHARACTERISTICS:
        (A) LENGTH: 24 amino acids
        (B) TYPE: amino acid
        (C) STRANDEDNESS: single (D) TOPOLOGY: unknown (ii) MOLECULE TYPE: peptide (iii) HYPOTHETICAL: YES (xi) SEQUENCE DESCRIPTION: SEQ ID NO:13:

Leu Ser Cys Ile Met Thr Leu Pro Cys Tyr Gln Glu Met Gly Leu Gly
1               5                  10                  15

Arg Phe Leu Ile Asp Ile Ser Tyr
            20

(2) INFORMATION FOR SEQ ID NO:14:

(i) SEQUENCE CHARACTERISTICS:
           (A) LENGTH: 24 amino acids
           (B) TYPE: amino acid
           (C) STRANDEDNESS: single
           (D) TOPOLOGY: unknown (ii) MOLECULE TYPE: peptide (iii) HYPOTHETICAL: YES (xi) SEQUENCE DESCRIPTION: SEQ ID NO:14:

Ile Ser Gln Phe Leu Ile Phe Pro Pro Tyr Gln Asn Lys Gly His Gly
1               5                  10                  15

Ser Cys Leu Tyr Glu Ala Ile Ile
            20

(2) INFORMATION FOR SEQ ID NO:15:

(i) SEQUENCE CHARACTERISTICS:
           (A) LENGTH: 24 amino acids
           (B) TYPE: amino acid
           (C) STRANDEDNESS: single
           (D) TOPOLOGY: unknown (ii) MOLECULE TYPE: peptide (iii) HYPOTHETICAL: YES (xi) SEQUENCE DESCRIPTION: SEQ ID NO:15:

Leu Phe Asn Ile Ala Val Asp Pro Asp Tyr Gln Arg Gln Gly Leu Gly
1               5                  10                  15

Arg Ala Leu Leu Glu His Leu Ile
            20

(2) INFORMATION FOR SEQ ID NO:16:

(i) SEQUENCE CHARACTERISTICS:
           (A) LENGTH: 24 amino acids
           (B) TYPE: amino acid
           (C) STRANDEDNESS: single
           (D) TOPOLOGY: unknown (ii) MOLECULE TYPE: peptide (iii) HYPOTHETICAL: YES (xi) SEQUENCE DESCRIPTION: SEQ ID NO:16:

Leu Phe Asn Ile Ala Ile Leu Pro Thr Tyr Gln Gly Cys Gly Phe Gly
1               5                  10                  15

Lys Leu Leu Leu Gly Lys Leu Ile
            20

(2) INFORMATION FOR SEQ ID NO:17:

(i) SEQUENCE CHARACTERISTICS:
            (A) LENGTH: 24 amino acids
            (B) TYPE: amino acid
            (C) STRANDEDNESS: single
            (D) TOPOLOGY: unknown (ii) MOLECULE TYPE: peptide (iii) HYPOTHETICAL: YES (xi) SEQUENCE DESCRIPTION: SEQ ID NO:17:

Val Ala Phe Leu Ala Val Thr Ala Asn Glu Gln Val Arg Gly Tyr Gly
1               5                  10                  15

Thr Arg Leu Met Asn Lys Phe Lys
            20

(2) INFORMATION FOR SEQ ID NO:18:

(i) SEQUENCE CHARACTERISTICS:
            (A) LENGTH: 24 amino acids
            (B) TYPE: amino acid
            (C) STRANDEDNESS: single
            (D) TOPOLOGY: unknown (ii) MOLECULE TYPE: peptide (iii) HYPOTHETICAL: YES (xi) SEQUENCE DESCRIPTION: SEQ ID NO:18:

Ile Val Phe Cys Ala Ile Ser Ser Thr Glu Gln Val Arg Gly Tyr Gly
1               5                  10                  15

Ala His Leu Met Asn His Leu Lys
            20

(2) INFORMATION FOR SEQ ID NO:19:

(i) SEQUENCE CHARACTERISTICS:
            (A) LENGTH: 24 amino acids
            (B) TYPE: amino acid
            (C) STRANDEDNESS: single
            (D) TOPOLOGY: unknown (ii) MOLECULE TYPE: peptide (iii) HYPOTHETICAL: YES (xi) SEQUENCE DESCRIPTION: SEQ ID NO:19:

Ile Val Phe Cys Ala Val Thr Ser Asn Glu Gln Val Lys Gly Tyr Gly
1               5                  10                  15

Thr His Leu Met Asn His Leu Lys
            20

(2) INFORMATION FOR SEQ ID NO:20:

(i) SEQUENCE CHARACTERISTICS:
            (A) LENGTH: 24 amino acids
            (B) TYPE: amino acid
            (C) STRANDEDNESS: single
            (D) TOPOLOGY: unknown (ii) MOLECULE TYPE: peptide (iii) HYPOTHETICAL: YES (xi) SEQUENCE DESCRIPTION: SEQ ID NO:20:

Ile Thr Ser Leu Ser Val Met Arg Thr Tyr Arg Arg Met Gly Ile Ala
1               5                  10                  15

Glu Asn Leu Met Arg Gln Ala Leu
            20

(2) INFORMATION FOR SEQ ID NO:21:

(i) SEQUENCE CHARACTERISTICS:
        (A) LENGTH: 24 amino acids
        (B) TYPE: amino acid
        (C) STRANDEDNESS: single
        (D) TOPOLOGY: unknown (ii) MOLECULE TYPE: peptide (iii) HYPOTHETICAL: YES (xi) SEQUENCE DESCRIPTION: SEQ ID NO:21:

```
Ile Gly Met Leu Ala Val Glu Ser Thr Tyr Arg Gly His Gly Ile Ala
1               5                   10                  15

Lys Lys Leu Val Glu Ile Ala Ile
            20
```

(2) INFORMATION FOR SEQ ID NO:22:

(i) SEQUENCE CHARACTERISTICS:
        (A) LENGTH: 24 amino acids
        (B) TYPE: amino acid
        (C) STRANDEDNESS: single
        (D) TOPOLOGY: unknown (ii) MOLECULE TYPE: peptide (iii) HYPOTHETICAL: YES (xi) SEQUENCE DESCRIPTION: SEQ ID NO:22:

```
Glu Glu Lys Ile Tyr Leu Asn Arg Gly Lys Gln Leu Ile Gly Met Gly
1               5                   10                  15

Glu Pro Asp Glu Ser Lys Val Ile
            20
```

(2) INFORMATION FOR SEQ ID NO:23:

(i) SEQUENCE CHARACTERISTICS:
        (A) LENGTH: 308 amino acids
        (B) TYPE: amino acid
        (C) STRANDEDNESS: single
        (D) TOPOLOGY: unknown (ii) MOLECULE TYPE: peptide (iii) HYPOTHETICAL: YES (xi) SEQUENCE DESCRIPTION: SEQ ID NO:23:

```
Lys Thr Val Ala Asp Arg Thr Lys Asp Val Ala Tyr Ser Phe Ser Asp
1               5                   10                  15

Pro Ile Leu Ser Thr Gln Leu Arg Thr Pro Pro Gln Pro Thr Ser
            20                  25                  30

Ile Arg Tyr Leu Tyr Phe Gly Thr Tyr Arg Ile Lys Pro Trp Tyr Thr
                35                  40                  45

Ser Pro Tyr Pro Glu Glu Tyr Ser Cys Ala Lys Asn Leu Tyr Ile Cys
            50                  55                  60

Glu Ser Cys Leu Lys Tyr Met Asn Ser Asp His Val Leu Gln Arg His
65                  70                  75                  80

Lys Met Lys Cys Ser Trp Ser Tyr Pro Pro Gly Asp Glu Ile Tyr Arg
                85                  90                  95

Asp Lys Asn Ile Ser Ile Phe Glu Val Asp Gly Gln Arg Gln Pro Ile
            100                 105                 110

Tyr Cys Gln Asn Leu Cys Leu Leu Ala Lys Met Phe Leu His Ser Lys
```

```
                     115                 120                 125
Met Leu Tyr Tyr Asp Val Glu Pro Phe Leu Phe Tyr Val Leu Thr Glu
    130                 135                 140

Phe Asp Gly Gln Glu Cys Lys Val Ile Gly Tyr Phe Ser Lys Glu Lys
145                 150                 155                 160

Arg Ser Ala Ser Asp Tyr Asn Val Ser Cys Ile Leu Thr Leu Pro Ile
                165                 170                 175

Tyr Gln Arg Arg Gly Tyr Gly Val Phe Leu Ile Asp Phe Ser Tyr Leu
            180                 185                 190

Leu Thr Gln Val Glu Gly Lys Leu Gly Ser Pro Glu Lys Pro Leu Ser
        195                 200                 205

Asp Leu Gly Leu Val Thr Tyr Arg Ser Tyr Trp Lys Met Arg Val Ala
    210                 215                 220

Lys Ala Leu Leu Glu Ile Thr Thr Pro Ile Ser Ile Asn Ala Ile Ala
225                 230                 235                 240

Lys Ser Thr Ser Met Val Cys Asp Val Ile Ser Thr Leu Glu Ser
                245                 250                 255

Leu Ser Val Phe Lys Tyr Asp Pro Leu Lys Lys Tyr Val Leu Gln
            260                 265                 270

Leu Lys Arg Asp Glu Leu Glu Asn Val Tyr Lys Ala Trp Asn Ile Lys
            275                 280                 285

His Pro Gln Arg Val Asn Pro Lys Leu Leu Arg Trp Thr Pro Tyr Leu
    290                 295                 300

Gly Glu Glu Gln
305

(2) INFORMATION FOR SEQ ID NO:24:

(i) SEQUENCE CHARACTERISTICS:
        (A) LENGTH: 299 amino acids
        (B) TYPE: amino acid
        (C) STRANDEDNESS: single
        (D) TOPOLOGY: unknown (ii) MOLECULE TYPE: peptide (iii) HYPOTHETICAL: YES (xi) SEQUENCE DESCRIPTION: SEQ ID NO:24:

Met Thr Gly Ser Leu Val Ser Asp Arg Ser His Asp Ile Val Thr
1               5                   10                  15

Arg Met Lys Asn Ile Glu Cys Ile Glu Leu Gly Arg His Arg Leu Lys
                20                  25                  30

Pro Trp Tyr Phe Ser Pro Tyr Pro Gln Glu Leu Thr Thr Leu Pro Val
            35                  40                  45

Leu Tyr Leu Cys Glu Phe Cys Leu Lys Tyr Gly Arg Ser Leu Lys Cys
50                  55                  60

Leu Gln Arg His Leu Thr Lys Cys Asp Leu Arg His Pro Pro Gly Asn
65                  70                  75                  80

Glu Ile Tyr Arg Lys Gly Thr Ile Ser Phe Phe Glu Ile Asp Gly Arg
                85                  90                  95

Lys Asn Lys Ser Tyr Ser Gln Asn Leu Cys Leu Leu Ala Lys Cys Phe
                100                 105                 110

Leu Asp His Lys Thr Leu Tyr Tyr Asp Thr Asp Pro Phe Leu Phe Tyr
            115                 120                 125

Val Met Thr Glu Tyr Asp Cys Lys Gly Phe His Ile Val Gly Tyr Phe
            130                 135                 140
```

```
Ser Lys Glu Lys Glu Ser Thr Glu Asp Tyr Asn Val Ala Cys Ile Leu
145                 150                 155                 160

Thr Leu Pro Pro Tyr Gln Arg Arg Gly Tyr Arg Lys Leu Leu Ile Glu
                165                 170                 175

Phe Ser Tyr Glu Leu Ser Lys Val Glu Gly Lys Thr Gly Thr Pro Glu
            180                 185                 190

Lys Pro Leu Ser Asp Leu Gly Leu Leu Ser Tyr Arg Ser Tyr Trp Ser
        195                 200                 205

Gln Thr Ile Leu Glu Ile Leu Met Gly Leu Lys Ser Glu Ser Gly Glu
    210                 215                 220

Arg Pro Gln Ile Thr Ile Asn Glu Ile Ser Glu Ile Thr Ser Ile Lys
225                 230                 235                 240

Lys Glu Asp Val Ile Ser Thr Leu Gln Tyr Leu Asn Leu Ile Asn Tyr
                245                 250                 255

Tyr Lys Gly Gln Tyr Ile Leu Thr Leu Ser Glu Asp Ile Val Asp Gly
            260                 265                 270

His Glu Arg Ala Met Leu Lys Arg Leu Leu Arg Ile Asp Ser Lys Cys
        275                 280                 285

Leu His Phe Thr Pro Lys Asp Trp Ser Lys Arg
290                 295
```

(2) INFORMATION FOR SEQ ID NO:25:

(i) SEQUENCE CHARACTERISTICS:
        (A) LENGTH: 310 amino acids
        (B) TYPE: amino acid
        (C) STRANDEDNESS: single
        (D) TOPOLOGY: unknown (ii) MOLECULE TYPE: peptide (iii) HYPOTHETICAL: YES (xi) SEQUENCE DESCRIPTION: SEQ ID NO:25:

```
Glu Ile Met Thr Glu Lys Asp Met Glu Leu Phe Arg Asp Ile Gln Glu
1               5                   10                  15

Gln Ala Leu Gln Lys Val Gly Val Thr Gly Pro Asp Pro Gln Val
            20                  25                  30

Arg Cys Pro Ser Val Ile Glu Phe Gly Lys Tyr Glu Ile His Thr Trp
            35                  40                  45

Ile Ser Ser Pro Tyr Pro Gln Glu Tyr Ser Arg Leu Pro Lys Leu Tyr
50                  55                  60

Leu Cys Glu Phe Cys Leu Lys Tyr Met Lys Ser Arg Thr Ile Leu Gln
65                  70                  75                  80

Gln His Met Lys Lys Cys Gly Trp Phe His Pro Pro Ala Asn Glu Ile
                85                  90                  95

Tyr Arg Lys Asn Asn Ile Ser Val Phe Glu Val Asp Gly Asn Val Ser
            100                 105                 110

Thr Ile Tyr Cys Gln Asn Leu Cys Leu Leu Ala Lys Leu Phe Leu Asp
        115                 120                 125

His Lys Thr Leu Tyr Tyr Asp Val Glu Pro Phe Leu Phe Tyr Val Leu
    130                 135                 140

Thr Gln Asn Asp Val Lys Gly Cys His Leu Val Gly Tyr Phe Ser Lys
145                 150                 155                 160

Glu Lys His Cys Gln Gln Lys Tyr Asn Val Ser Cys Ile Met Ile Leu
                165                 170                 175

Pro Gln Tyr Gln Arg Lys Gly Tyr Gly Arg Phe Leu Ile Asp Phe Ser
            180                 185                 190
```

```
Tyr Leu Leu Ser Lys Arg Glu Gly Gln Ala Gly Ser Pro Glu Lys Pro
        195             200             205

Leu Ser Asp Leu Gly Arg Leu Ser Tyr Met Ala Tyr Trp Lys Ser Val
        210             215             220

Ile Leu Glu Cys Leu Tyr His Gln Asn Asp Lys Gln Ile Ser Ile Lys
225             230             235             240

Lys Leu Ser Lys Leu Thr Gly Ile Cys Pro Gln Asp Ile Thr Ser Thr
                245             250             255

Leu His His Leu Arg Met Leu Asp Phe Arg Ser Asp Gln Phe Val Ile
            260             265             270

Ile Arg Arg Glu Lys Leu Ile Gln Asp His Met Ala Lys Leu Gln Leu
        275             280             285

Asn Leu Arg Pro Val Asp Val Asp Pro Glu Cys Leu Arg Trp Thr Pro
        290             295             300

Val Ile Val Ser Asn Ser
305             310
```